(12) United States Patent
Umeda et al.

(10) Patent No.: US 6,342,516 B1
(45) Date of Patent: Jan. 29, 2002

(54) PHENYLAZOLE COMPOUNDS, PROCESS FOR PRODUCING THE SAME AND DRUGS FOR HYPERLIPEMIA

(75) Inventors: Nobuhiro Umeda; Nobuo Mochizuki, both of Odawara; Seiichi Uchida, Naka-gun; Tadayuki Nishibe, Hiratsuka; Hirokazu Yamada; Kunihito Ito, both of Odawara; Hiromi Horikoshi, Sapporo, all of (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 09/744,786

(22) PCT Filed: Jul. 29, 1999

(86) PCT No.: PCT/JP99/04070

§ 371 Date: Jan. 26, 2001

§ 102(e) Date: Jan. 26, 2001

(87) PCT Pub. No.: WO00/06550

PCT Pub. Date: Feb. 10, 2000

(30) Foreign Application Priority Data

| Jul. 31, 1998 | (JP) | 10-218316 |
| Aug. 5, 1998 | (JP) | 10-222157 |
| Jan. 26, 1999 | (JP) | 11-16846 |
| Jan. 28, 1999 | (JP) | 11-19670 |
| Feb. 1, 1999 | (JP) | 11-24318 |

(51) Int. Cl.[7] .............. C07D 233/58; C07D 231/12; A61K 31/4155; A61K 31/4178; A61P 1/16

(52) U.S. Cl. .............. 514/397; 514/406; 548/311.1; 548/312.1

(58) Field of Search .......... 548/311.1, 312.1, 548/375.1; 514/397, 406

(56) References Cited

U.S. PATENT DOCUMENTS

| 4,301,169 A | 11/1981 | Yamanaka et al. |
| 4,675,319 A | 6/1987 | Nardi et al. |
| 5,128,335 A | 7/1992 | Guthikonda et al. |
| 5,128,351 A | 7/1992 | Wissner |
| 5,180,742 A | 1/1993 | Terao et al. |
| 5,272,180 A | 12/1993 | Hashimoto et al. |
| 5,374,643 A | 12/1994 | Atwal et al. |
| 6,133,279 A | 10/2000 | Cynshi et al. |

FOREIGN PATENT DOCUMENTS

| DE | 2525024 | 12/1976 |
| DE | 3407505 | 5/1985 |
| EP | 345593 | 6/1988 |
| EP | 483772 | 5/1992 |
| JP | 61-44840 A | 3/1986 |
| JP | 2-121975 | 5/1990 |
| JP | 3-141258 | 7/1998 |
| JP | 10-182459 | 7/1998 |
| WO | 95/29163 | 11/1995 |
| WO | WO 98/50358 | 11/1998 |
| WO | WO 98/57937 | 12/1998 |

OTHER PUBLICATIONS

Amer. Oil. Chemists Soc., 51, pp 200–203 (1974).
Collection czechoslov. Chem. Commun., 24, pp 1689–1694 (1959) (no English translation available).
J. Org. Chem., 54, pp 560–569 (1989).
J. Med. Chem., 33, pp 1491–1496 (1990).
J. Org. Chem., 54, pp 3303–3310 (1989).
J. Med. Chem., 32, pp 2214–2221 (1989).
Chem. Pharm. Bull., 30, pp 2797–2819 (1982).

*Primary Examiner*—Deborah C. Lambkin
*Assistant Examiner*—Andrea M. D'Souza
(74) *Attorney, Agent, or Firm*—Dennis G. LaPointe; Mason & Associates, P.A.

(57) ABSTRACT

Phenylazole compounds represented by general formula (1) or pharmaceutically acceptable salts thereof and drugs for hyperlipemia which contain these compounds as the active ingredient, wherein A represents imidazolyl, pyrazolyl, etc.; B represents (1*a*) or (1*b*) (wherein $R^2$ and $R^3$ represent each hydrogen, $C_{1-6}$ alkyl, etc; and k is 0 or an integer of 1 to 15); Y represents O, S, a bond, etc.; and Z represents an optionally substituted and saturated or unsaturated heterocycle containing 1 to 4 N, O or S atoms. Among all, compounds wherein Z is substituted chroman-2-yl, 2,3-dihydrobenzofuran-2-yl, etc. have an effect of inhibiting the formation of lipid peroxides too.

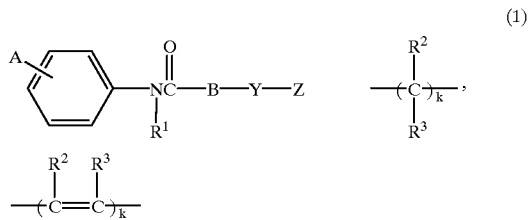

7 Claims, No Drawings

PHENYLAZOLE COMPOUNDS, PROCESS FOR PRODUCING THE SAME AND DRUGS FOR HYPERLIPEMIA

This application is a 371 of PCT/JP99/04070 filed Jul. 29, 1999.

FIELD OF INVENTION

The present invention is directed to phenylazole compounds, processes for producing the phenylazole compounds and drugs for hyperlipemia containing the said phenylazole compounds as the active ingredients.

BACKGROUND ART

Serious heart diseases, such as myocardial infarction, are a disease induced by hyperlipemia which is the primary factor causing of arteriosclerosis. Presently, three types of hyperlipemia have been known, which contain a type that raises the concentration of triglyceride known as a lipid in blood, a type that raises the concentration of cholesterol in blood, and a type that raises both triglyceride and cholesterol in blood. Since remedy of hyperlipemia is important for prevention of myocardial infarction, development for finding new drugs for hyperlipemia provided with excellent activity and safeness is desired.

As the representative drugs for hyperlipemia, pravastatin, simvastatin, clofibrate-type drugs, etc. have been known. However, these drugs are not the one that can reduce the lipid in blood and cholesterol simultaneously and to an equivalent level.

Although a drug which can reduce the amount of triglyceride in blood and cholesterol simultaneously and to an equivalent level and has an effect to prevent peroxidized lipid production has been strongly required in view of remedy and prevention of disease, such as ischemic heart disease induced by arteriosclerosis, myocardial infarction and cerebral infarction, no drug having such effect has been found yet.

Recently, on the other hand, it has been reported that intravital formation of peroxidized lipids and the associating radical reactions thereto give various baneful influence to living organisms via damage to the membranes, cells and the like. Accordingly, various antioxidants and preventing agents for peroxidized lipids production have been tested in order to apply them as a drug for preventing such baneful influence, and research to develop antioxidant drugs have been performed basing upon the chemical structures of the antioxidants and the preventing agents for peroxidized lipids production.

Such antioxidant drugs have been reported, for examples, in J. Amer. Oil Chemists, Soc. 51, 200–203 (1974), JP Laid-opened No. Sho 61-44840, JP Laid-opened No. Hei 1-104033, JP Laid-opened No. 2-121975, EP No. 345593, EP No. 483772, etc., however, the drugs disclosed in these references have problems of insufficient antioxidant effect and unacceptable side effects, and they are not exactly allowable to be used practically.

As the similar compounds to the compounds of the present invention, imidazolylphenyl derivatives, which have an effect to inhibit cholesterol biosynthesis, are disclosed in WO 95/29163.

Further, compounds represented by the following chemical structure are disclosed in DE No. 3,407,505 as a cure for arthritis.

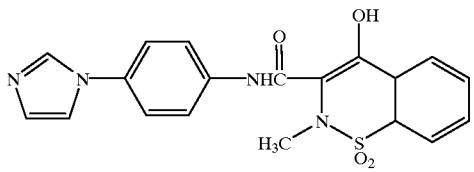

In addition, although carbonylaminophenylimidazole derivatives are disclosed in JP Laid-opened No. Sho 55-69567 gazette, EP No. 324377 gazette and EP No. 458037 gazette, there is no compound which has an effect to reduce the concentration of lipids in blood, and no cyclic carbonylaminophenylazole compound identical to the compounds of the present invention has been reported.

DISCLOSURE OF THE INVENTION

It is an object of the present invention to provide a drug capable of reducing more amount of triglyceride and cholesterol in blood simultaneously and to an equivalent level than the effect given by conventional drugs and further having an effect to prevent peroxidized lipids production.

After giving investigation to achieve such purpose by the inventors of the present invention, compounds having an effect to remarkably reduce the amounts of triglyceride and cholesterol in blood simultaneously and to an equivalent level were found, and the compounds further having anti-oxidant effect and an effect to prevent peroxidized lipids production were also found, which thereby constituting the present invention.

The present invention is directed to; (a) phenylazole compounds represented by a general formula (1) and pharmaceutically acceptable salts thereof;

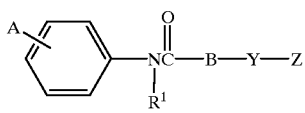

(1)

wherein $R^1$ represents hydrogen or optionally substituted $C_{1-6}$ alkyl,

A represents imidazolyl optionally substituted with a group represented by following formulas shown below or optionally substituted pyrazolyl,

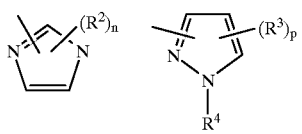

wherein $R^2$ and $R^3$ each independently represent optionally substituted $C_{1-6}$ alkyl, $R^4$ represents optionally substituted $C_{1-6}$ alkyl, $C_{1-6}$ alkylcarbonyl or benzoyl, n represents 0 or an integer of 1–3, p represents 0 or an integer of 1–2, and when both n and p are an integer of 2 or more, $R^2$ and $R^3$ may be the same or different, B represents a group represented by either of the following chemical structures;

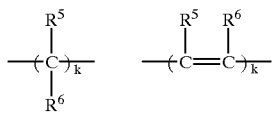

wherein $R^5$ and $R^6$ each independently represent hydrogen, cyano, hydroxy, halogeno, $C_{1-6}$ alkyl, $C_{1-6}$ alkoxy, $C_{2-6}$ alkenyl, $C_{2-6}$ alkynyl, $C_{2-6}$ alkenyloxy, $C_{2-6}$ alkynyloxy, $C_{1-6}$ acyloxy, $C_{3-6}$ cycloalkyl, or optionally substituted phenyl, k represents 0 or an integer of 1–15, provided, $R^5$ and $R^6$ may be the same or different when k is an integer of 2 or more;

Y represents a bonding, or O, S, $SO_2$, CO, $OCH_2$, $N(R^7)CO$ or $N(R^7)$, wherein $R^7$ represents hydrogen or optionally substituted $C_{1-6}$ alkyl;

Z represents a saturated or unsaturated heterorcyclic group containing 1–4 optionally substituted N, optionally substituted O or optionally substituted S, optionally substituted benzoquinonyl or optionally substituted naphthoquinonyl;

(b) the compounds represented by the general formula (1) described above, wherein Z represents optionally substituted chroman-2-yl, optionally substituted 2,3-dihydrobenzofuran-2-yl, optionally substituted thiochroman-2-yl, optionally substituted 2,3-dihydrobenzothiophen-2-yl, optionally substituted 1,3-benzoxathiol-2-yl, optionally substituted 1,4-benzoquinon-2-yl or optionally substituted 1,4-naphthoquinon-2-yl;

(c) the compounds represented by the general formula (1) described above, wherein Z is a group represented by any of chemical structures (A), (B) and (C) shown below:

(A)

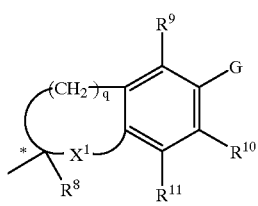

(B)

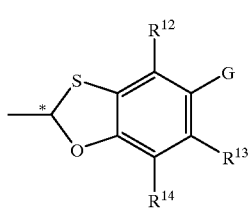

(C)

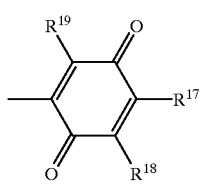

wherein * represents asymmetric carbon atom, $X^1$ represents oxygen or sulfur, and q represents an integer of 1 or 2, $R^8$, $R^9$, $R^{12}$, $R^{13}$ and $R^{14}$ each independently represent hydrogen or $C_{1-6}$ alkyl, and $R^{10}$ and $R^{11}$ each independently represent hydrogen, $C_{1-6}$ alkyl or $C_{1-6}$ alkoxy, G represents a group represented by either formula of $OR^{15}$ or $NHR^{16}$, wherein $R^{15}$ and $R^{16}$ each represent hydrogen, $C_{1-6}$ alkylcarbonyl or optionally substituted benzoyl, $R^{17}$ and $R^{18}$ each independently represent hydrogen, methyl or methoxy, or $R^{17}$ and $R^{18}$ may form a ring in together represented by a formula, #—$CH_2CH_2CH_2$—#, "—$CH_2CH=CH$—#, #—CH=$CHCH_2$—#, #—$CH_2$CH_2CH_2CH_2$—#, or #—CH=CHCH=CH—#, wherein # represents that these groups are bonding to a quinone ring at the bonding site of $R^{17}$ and $R^{18}$, and $R^{19}$ represents hydrogen or methyl;

(d) the compounds represented by the general formula (1) described above, wherein Z represents an optionally substituted heterocyclic group, which is furyl, thienyl, pyrrolyl, imidazolyl, thiazolyl, oxazolyl, pyridyl, pyrimidinyl, pyrazinyl, pyridazinyl, dihydropyridazinyl, pyrazolyl, tetrahydrofuranyl, tetrahydrothienyl, pyrrolidinyl, pyranyl, thiopyranyl, piperidinyl, flavonyl, dithiolanyl, benzofuranyl, benzothiophenyl, quinolyl, isoquinolyl, quinoxalinyl, benzthiazolyl, benzoxazolyl, benzoxadinyl, benzimidazolyl, indolyl, indazolyl, 3,4-methylenedioxyphenyl, dihydrofuranopyrimidinyl, dihydrothienopyrimidinyl, dihydropyrrolopyrimidinyl, camphanyl, tetrahydrothianaphthenyl, cyclopenta [2,1-f] indolinyl, imidazopyrimidinyl, pyrrolopyridyl, furanopyridyl or xanthinyl;

(e) the compounds represented by the general formula (1) described above, wherein Z is an optionally substituted heterocyclic group, wherein the substituents are same or different ones selected from a group consisting of hydroxy, nitro, halogeno, $C_{1-6}$ alkyl, $C_{1-6}$ alkoxy, $C_{1-6}$ haloalkyl, optionally subituted phenyl, optionally substituted benzyl $C_{1-6}$ alkylsulfonyl or oxo;

(f) the compounds represented by the general formula (1) described above, wherein A is 1-imidazolyl or 1H-pyrazol-5-yl to be substituted at the 4th position of the benzene ring;

(g) a process to produce the compounds represented by the general formula (1) described above, characterized in that the compounds are produced by dehydrating and condensing an amine compound represented by a general formula (2);

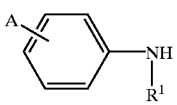 (2)

wherein A and $R^1$ are as defined above, and a carboxylic acid represented by a general formula (3);

HOOC-B-Y-Z (3)

wherein Y and Z are as defined above; (h) a process to produce compounds represented by a general formula (1');

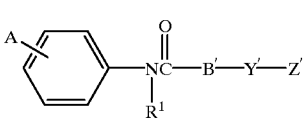 (1')

wherein A is as defined above, and B', Y' and Z' are respectively as defined for B, Y and Z except halogenated groups with a halogenating agent, such as hydroxy and amino, by halogenating a carboxylate compound represented by a general formula (3');

HOOC-B'-Y'-Z' (3')

wherein B', Y' and Z' are as defined above, to prepare an acid chloride represented by a general formula (4);

CIOC-B'-Y'-Z'     (4)

wherein B', Y' and Z' are as defined above, and subjecting the obtained acid chloride to a reaction with an amine represented by the general formula (2); and (i) drugs for hyperlipemia containing one or more compounds represented by the general formula (1) described above and/or the pharmaceutically acceptable salts thereof as the active pharmaceutical ingredient.

BEST MODE FOR CARRYING OUT THE INVENTION

In the general formula (1) described above, $C_{1-6}$ alkyl, such as methyl, ethyl, propyl, isopropyl, butyl, isobutyl, s-butyl and t-butyl, is given for $R^1$, however, it is preferable to give either hydrogen or methyl for $R^1$.

For A, imidazolyl or pyrazolyl each represented by the following chemical formula is given;

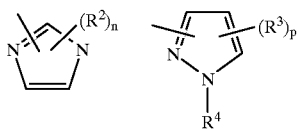

and in the formula, as the $C_{1-6}$ alkyl represented by $R^2$, $R^3$ and $R^4$, methyl ethyl, propyl, isopropyl, butyl, isobutyl, s-butyl, t-butyl and the like can be given. Further, these $C_{1-6}$ alkyls may be substituted by halogeno, such as chlorine, bromine, fluorine and iodine, and the like.

As examples for $C_{1-6}$ alkylcarbonyl specified for $R^4$, acetyl, propionyl, butylyl, isobutylyl, valeryl, pivaloyl, etc. can be given.

In addition, for the pyrazolyl, the tautomerism structures shown below may be given, when $R^4$ is hydrogen.

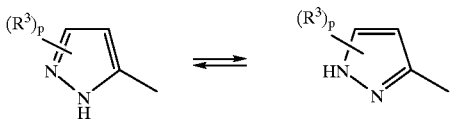

As A described above, 1-imidazolyl, 1H-pyrazol-5-yl, 1H-pyrazol-4-yl, 1-methylpyrazol-5-yl, 1-methylpyrazol-3-yl and 1-benzylpyrazol-4yl are preferably given.

$R^5$ and $R^6$ in B defined above each independently represent hydrogen, cyano, hydroxy, halogeno, such as chlorine, bromine, fluorine and iodine, $C_{1-6}$ alkyl, such as methyl, ethyl, propyl, isopropyl, butyl, isobutyl, s-butyl and t-butyl, $C_{1-6}$ alkyl optionally substituted with halogeno, such as chlorine, bromine, fluorine and iodine, $C_{1-6}$ alkoxy, such as methoxy, ethoxy, propoxy and isopropoxy, or the like, $C_{1-6}$ alkoxy, such as methoxy, ethoxy, propoxy, isopropoxy and butoxy, $C_{2-6}$ alkenyl, such as ethenyl, 1-propenyl, 1-methylvinyl, allyl, 1methylallyl and 2-butenyl, $C_{2-6}$ alkynyl, such as ethynyl, 1-propynyl and 2-propynyl, $C_{2-6}$ alkenyloxy, such as ethenyloxy, 1-propenyloxy, 1-methylvinyloxy, allyloxy, 1-methylallyloxy and 2-butenyloxy, $C_{2-6}$ alkynyloxy, such as ethynyloxy, 1-propynyloxy and 2-propynyloxy, $C_{1-6}$ acyloxy, such as acetoxy, propynyloxy and butylyloxy, $C_{3-6}$ cycloalkyl, such as cyclopropyl, cyclobutyl, cyclopentyl and cyclohexyl, or phenyl optionally having substituents at the arbitrary positions on the benzene ring.

As the substituent for the phenyl described above, nitro, halogeno, such as chlorine, bromine, fluorine and iodine, $C_{1-6}$ alkyl, such as methyl, ethyl, propyl, isopropyl, butyl, isobutyl, s-butyl and t-butyl, $C_{1-6}$ alkoxy, such as methoxy, ethoxy, propoxy, isopropoxy and butoxy, and $C_{1-6}$ haloalkyl, such as chloromethyl, dichloromethyl, trichloromethyl, trifluoromethyl, 1-fluoroethyl, 1,1-difluoroethyl and pentafluoroethyl, can be given.

k represents 0 or an integer of 1–15, and when k is 2 or more, plural numbers of $R^5$ and $R^6$ exist respectively, and these plural $R^5$ and $R^6$ may be same or different each other.

Among the groups exemplified for $R^5$ and $R^6$ in B described above, hydrogen, methyl and phenyl are preferable ones, and k is preferably 0, 1, 2, 3, 4 or 5.

Y is O, S, $SO_2$, CO, $OCH_2$, $N(R^7)$ CO or $N(R^7)$, and as examples for $R^7$, hydrogen, methyl, ethyl, propyl, isopropyl, butyl, s-butyl, t-butyl or $C_{1-6}$ alkyl optionally substituted with halogeno, such as chlorine, bromine, fluorine and iodine, or $C_{1-6}$ alkoxy, such as methoxy, ethoxy, propoxy and isopropoxy, can be given.

As examples for the groups represented by Z, the following cyclic groups can be given.

① Optionally substituted chroman-2-yl, optionally substituted 2,3-dihydrobenzofuran-2-yl, optionally substituted thiochroman-2-yl, optionally substituted 2,3-dihydrobenzothiophene-2-yl, or optionally substituted 1,3-benzoxathiol-2-yl.

As examples for the group represented by Z, groups represented by the following chemical formulas can be (A)

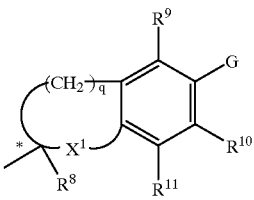

(B)

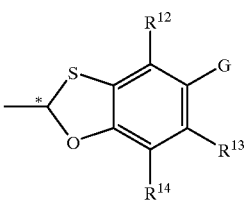

(C)

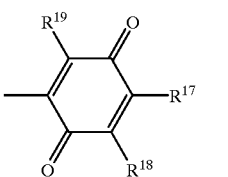

given.

wherein *, $X^1$ and q are as defined above.

$R^8$, $R^9$, $R^{12}$, $R^{13}$ and $R^{14}$ each independently represent hydrogen or $C_{1-6}$ alkyl, and $R^{10}$ and $R^{11}$ each represent hydrogen, $C_{1-6}$ alkyl or $C_{1-6}$ alkoxy.

As examples for the $C_{1-6}$ alkyl represented by $R^8$, $R^9$, $R^{10}$, $R^{11}$, $R^{12}$, $R^{13}$ and $R^{14}$, methyl, ethyl, propyl, isopropyl, butyl, isobutyl, s-butyl, t-butyl, etc. can be given.

As examples for the $C_{1-6}$ alkoxy represented by $R^{10}$ and $R^{11}$, methoxy, ethoxy, propoxy, isopropoxy, butoxy, etc. can be given.

G described above is preferably a group represented by a formula, $OR^{15}$, $NHR^{16}$ or the like, wherein $R^{15}$ and $R^{16}$ each independently represent hydrogen $C_{1-6}$ acyl or optionally substituted benzoyl. As examples for the $C_{1-6}$ alkylcarbonyl represented by $R^{15}$ and $R^{16}$, acetyl, propionyl, butylyl, isobutylyl, valeryl, isovaleryl, pivaloyl, etc. can be given. As examples for the substituent for the optionally substituted benzoyl described above, halogeno, such as fluorine, chlorine and bromine, $C_{1-6}$ alkyl, such as methyl and ethyl, $C_{1-6}$ alkoxy, such as methoxy, ethoxy and isopropoxy, nitro, cyano, etc., those which may be substituted at arbitrary positions on the benzene ring, can be given.

$R^{17}$ and $R^{18}$ each independently represented hydrogen, methyl or methoxy, or $R^{17}$ and $R^{18}$ may be associated to form a ring represented by a formula, $\#—CH_2CH_2CH_2—\#$, $\#—CH_2CH=CH—\#$, $\#—CH=CHCH_2—\#$, $\#—CH_2CH_2CH_2CH_2—\#$ or $\#—CH=CHCH=CH—\#$, wherein # represents that these groups are respectively bonding to quinone ring at the bonding site of $R^{17}$ and $R^{18}$, and $R^{19}$ represents hydrogen or methyl.

② As examples for the optionally substituted and saturated or unsaturated heterocyclic group containing 1-4 N, O or S atoms, groups represented by general formulas shown in the following can be given.

In the following formulas, there is no limitation for the substitution position of the heterocyclic group and of the substituents. In case that each heterocyclic group has more than 2 substituents, such substituents may be the same or different with each other.

Z1:

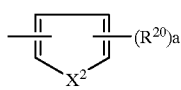

Z2:

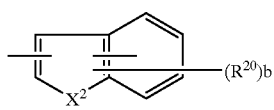

(A line passing through two rings of the fused ring represents that either ring may be substituted. The same definition shall be applied as well in the followings.)

Z3:

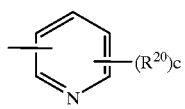

Z4:

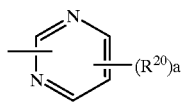

Z5:

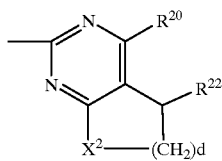

Z6:

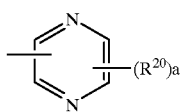

Z7:

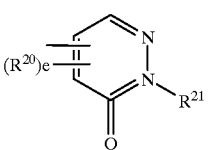

Z8:

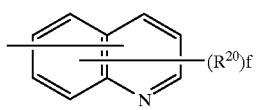

Z9:

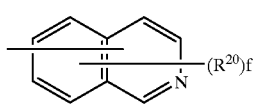

Z10:

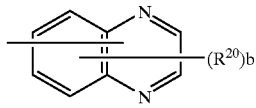

Z11:

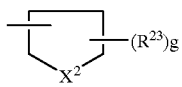

Z12:

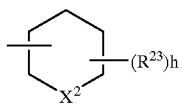

Z13:

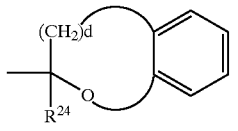

Z14:

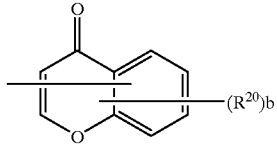

Z15:

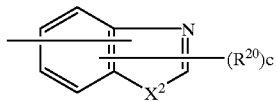

-continued
Z16:
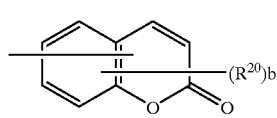
Z17:
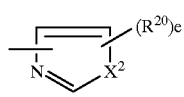
Z18:
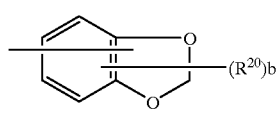
Z19:
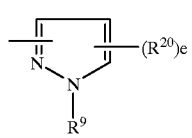
Z20:
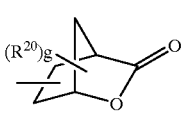
Z21:
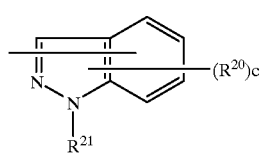
Z22:
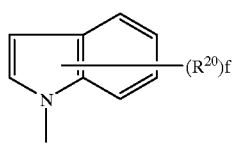
Z23:
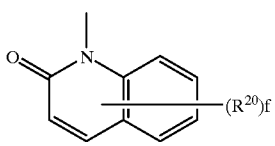
Z24:
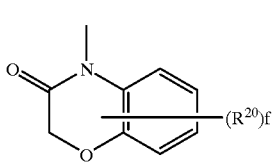
-continued
Z25:
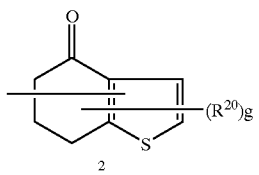
Z26:
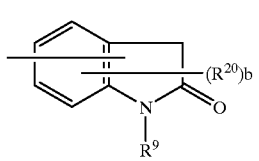
Z27:
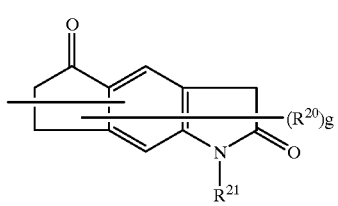
Z28:
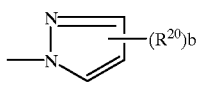
Z29:
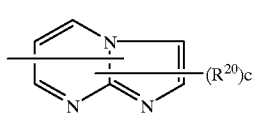
Z30:
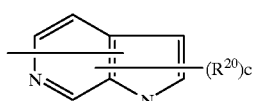
Z31:
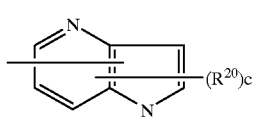
Z32:
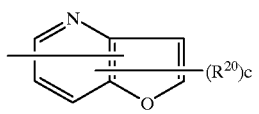
Z33:
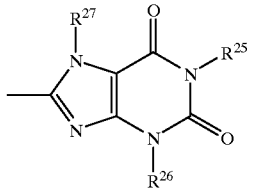

-continued

Z34:

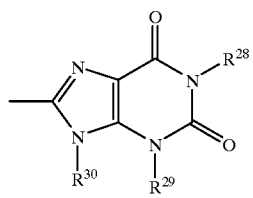

Z35:

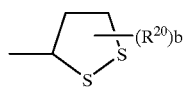

wherein $X^2$ represents $NR^{21}$, S or O, $R^{20}$ represents hydroxy, nitro, halogeno, $C_{1-6}$ alkyl, $C_{1-6}$ alkoxy, $C_{1-6}$ haloalkyl or optionally substituted phenyl, $R^{21}$ represents hydrogen, $C_{1-6}$ alkyl, $C_{1-6}$ haloalkyl or optionally substituted benzyl, $R^{22}$ represents hydroxy, halogeno, $C_{1-6}$ alkyl, $C_{1-6}$ alkoxy, $C_{1-6}$ haloalkyl or optionally substituted phenyl, $R^{23}$ represents hydroxy, oxo, halogeno, $C_{1-6}$ alkyl, $C_{1-6}$ alkoxy or $C_{1-6}$ haloalkyl, $R^{24}$, $R^{25}$, $R^{26}$, $R^{27}$, $R^{28}$, $R^{29}$ and $R^{30}$ each independently represent hydrogen, hydroxy, nitro, halogeno, $C_{1-6}$ alkyl, $C_{1-6}$ alkoxy or $C_{1-6}$ haloalkyl, a represents 0 or an integer of 1–3,
b represents 0 or an integer of 1–5,
c represents 0 or an integer of 1–4,
d represents an integer of 1 or 2,
e represents 0 or an integer of 1 or 2,
f represents 0 or an integer of 1–6,
g represents 0 or an integer of 1–7, and h represents 0 or an integer of 1–9.

The most preferable heterocycles among the heterocycles represented by Z1 through Z35 are the ones represented by Z2, Z3, Z4, Z8, Z22 and Z23.

The compounds of the present invention represented by the general formula (1) are produced, for example, according to the following processes.

Process 1

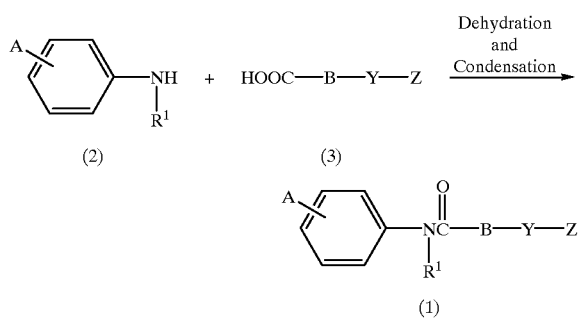

wherein A, B, $R^1$, Y and Z are as defined above.

This process is to obtain the objective compounds of the present invention, that is amide derivatives represented by a general formula (1), by dehydrating and condensing a carboxylate compound represented by a general formula (3) and an amine represented by a general formula (2) according to a commonly-known method.

This dehydrating and condensing reactions is carried out in the presence of an appropriate condensing agent. In this reaction, as the condensing agent, 1,3-dicyclohexylcarbodiimide, 1-(3-dimethylaminopropyl)-3-ethylcarbodiimide, 2-ethoxy-1-ethoxycarbonyl-1,2-dihydroquinoline and the like can be used, for example.

This reaction may be proceeded faster by means of coexistently using N-hydroxysuccinimide, 1-hydroxybenzotriazole, or 3,4-dihydro-3-hydroxy-4-oxo-1,2,3-benzotriazine.

As the solvent to be used in the reaction, any solvents which are inactive to the reaction can be used, and for examples, ethers, such as diethyl ether, tetrahydrofuran (THF) and 1,4-dioxane, aromatic hydrocarbons, such as benzene, toluene and xylene, halogenated hydrocarbons, such as dichloromethane, chloroform and 1,2-dichloroethane, acetonitrile, dimethylformamide (DMF), dimethylsulfoxide (DMSO), pyridine, etc. can be used as the said solvent.

The reaction is carried out under a temperature ranging from –15° C. to the boiling point of the solvent used, and preferably in a range of from 0 to 80° C.

Process 2

Among the compounds of the present invention, the compounds represented by the general formula (1), wherein the groups represented B, Y and Z are inactive against the halogenating agent, can be prepared according to the following reaction equation.

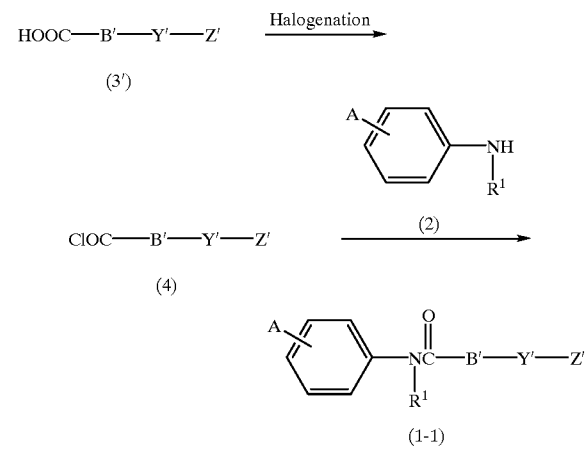

wherein A and $R^1$ are as defined above, B', Y' and Z' are as defined above for B, Y and Z except the groups, such as hydroxy and amino, which are sensitive to halogenation with a halogenating agent.

Namely, this reaction is to obtain an acid chloride (4) by subjecting a carboxylate derivative represented by a general formula (3') to a reaction with a halogenating agent, such as thionyl chloride, phosphorous pentachloride and oxalyl chloride oxalate, and then to subject the obtained acid chloride to a reaction with an amine represented by a general formula (2) in an inactive organic solvent and in the presence of a base.

As the solvent to be used in the reaction, any solvents inactive to the reaction can be used without limitation, ethers, such as diethyl ether, THF and 1,4-dioxane, aromatic hydrocarbons, such as benzene, toluene and xylene, halogenated hydrocarbons, such as dichloromethane, chloroform and 1,2-dichloroethane, acetonitrile, DMF, DMSO, pyridine, etc. can be used, for examples.

As the base to be used in the reaction described above, amines, such as triethylamine, pyridine and 1,8-diazabicyclo[5,4,0] undec-7-ene (DBU), and inorganic bases, such as sodium hydrogencarbonate, sodium carbonate, potassium carbonate and sodium hydroxide, can be used, for examples.

The reaction is carried out under a temperature ranging from −15° C. to the boiling point of the solvent used, and preferably at a temperature of from 0 to 80° C.

Process 3

Among the compounds specified in the present invention, the compounds of which part represented by Z is quinone ring derivative can be produced according to the following reaction formula.

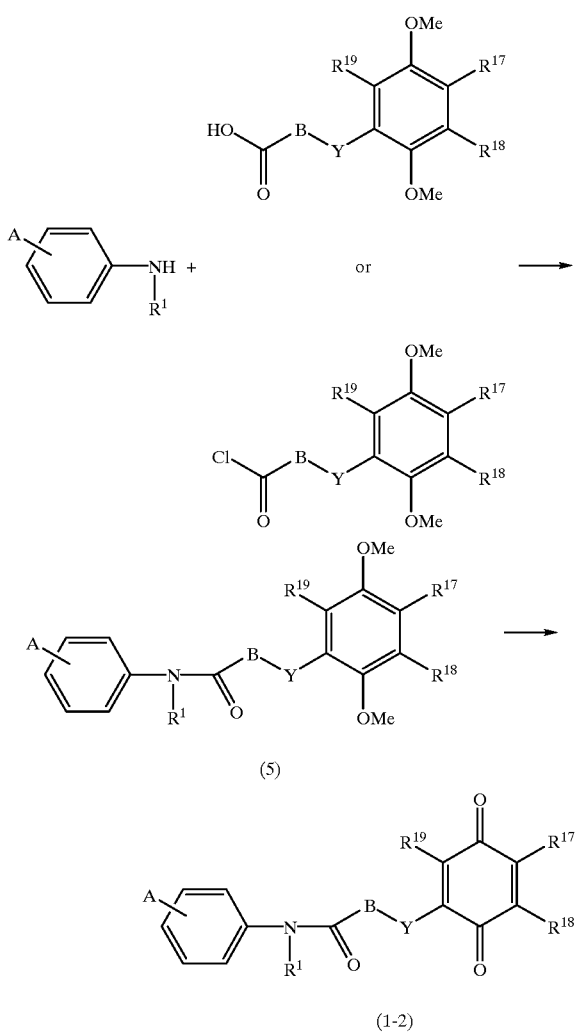

(5)

(1-2)

wherein A, B, $R^1$, $R^{17}$, $R^{18}$, $R^{19}$ and Y are as defined above.

The quinone derivatives represented by the general formula (1–2) can be prepared by producing the amide compound represented by the general formula (5) according to the same process described in the Process 1 to 2 and then subjecting the obtained amide compound to a reaction with an oxidizing agent.

As the said oxidizing agent, silver oxide, cerium ammonium nitrate or the like can be used. When silver oxide is used, the reaction is carried out in either water or water-contained organic solvent, such as dioxane and acetonitrile, in the presence of nitric acid under a reaction temperature of from −10° C. to 30° C. Whereas, when cerium ammonium nitrate is used as the oxidizing agent, the reaction is carried out in a water-contained organic solvent, such as methanol and acetonitrile, either alone or in the presence of pyridine-2,6-dicarboxylate N-oxide, pyridine-2,4,6-tricarboxylic acid, pyridine-2,6-dicarboxylic acid or the like. The said reaction is carried out under a reaction temperature of approximately from −5° C. to 20° C.

Among the carboxylic acid compounds represented by the general formula (3) described above, the compounds wherein the part represented by Y is bonding can be produced according to known processes reported in references, such as Collection Czechoslov. Chem. Commun., 24, 1689–1694 (1959), J. Amer. Oil Chemists' Soc., 51, 200–203 (1974), J. Org. Chem., 54, 561–569 (1989), J. Med. Chem., 33, 1491–1496 (1990), WO 97/49388, JP Laid-open No. Sho 61-44840 Gazette, J. Org. Chem., 54, 3303–3310 (1989), J. Med. Chem., 32, 2214–2221 (1989), and Chem. Pharm. Bull., 30, (8) 2797–2819 (1982).

The compounds represented by the general formula (3) wherein Y is $N(R^7)CO$ can be produced according to the following reaction process.

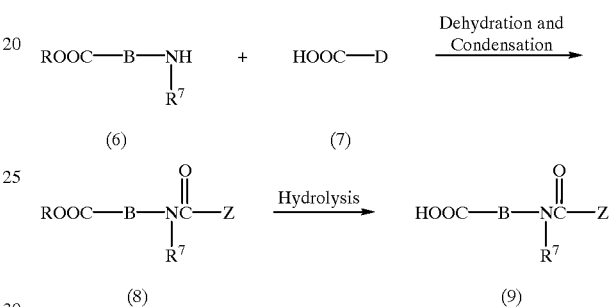

wherein B, Z and $R^7$ are as defined above.

Namely, the amide compounds represented by the general formula (8) is obtained by dehydrating and condensing the carboxylic acid derivative represented by the general formula (7) and an amine compound represented by the general formula (6) according to the same process as described in the Process 1. Then, the ester part of the compound represented by the general formula (8) is hydrolyzed according to a publicly-known process to obtain the carboxylic acid derivative represented by the general formula (9)

After the completion of the reaction, the objective compounds can be obtained by employing a common process for refining.

The chemical structures of the compounds specified in the present invention are determined by analytical means of IR, NMR, MS, etc.

Though optical isomers and tautomers may be produced in the compounds (1) of the present invention, and the materials compounds (3), (4) and (9), all of these isomers and tautomers fall within the scope of the compounds according to the present invention.

As pharmaceutically acceptable salts of the compounds represented by the general formula (1), salts of inorganic acids, such as chloric acid, sulfuric acid, nitric acid and phosphoric acid, and salts of organic acids, such as acetic acid, propionic acid, lactic acid, succinic acid, tartaric acid, citric acid, benzoic acid, salicylic acid, nicotinic acid and heptagluconic acid, are given as the examples. These salts can be easily prepared according to commonly-known synthetic processes.

(Drug for Hyperlipemia)

The compounds of the present invention strongly reduce the both amounts of triglyceride and cholesterol in blood to an equivalent level and are useful as drug for hyperlipemia.

Among the compounds of the present invention, the compounds represented by the general formula (1), wherein Z is optionally substituted chroman-2-yl, optionally substituted 2,3-dihydrobenzofuran-2-yl, optionally substituted thiochroman-2-yl, optionally substituted 2,3-dihydrobenzothiophen-2-yl, optionally substituted 1,3-benzoxathiol-2-yl, optionally substituted benzoquinonyl or optionally substituted naphthoquinonyl, have effects of anti-oxidizing and inhibiting the production of peroxidized lipids, and therefore, those compounds can inhibit the attack and development of arteriosclerosis by preventing the oxidative deformation of LDL, so that these compounds can be a remedy not only for arteriosclerosis but also for various diseases caused by oxidative effect, such as senile dementia, heart diseases, cancer, diabetes mellitus, gastral diseases, burn injury, ophthalmic diseases, and ranal diseases. In case of ishemic organ discases, such as cerebral apoplexy and myocardinal infarction, various active enzymes are generated at the time of blood reperfusion in an ishemic part, and tissues are further damaged due to destruction of cell membranes caused by peroxidized lipids formation reaction. The compounds of the present invention having an antioxidizing effect can be a remedy for ishemic organ disorder since those compounds can prevent to cause damage to tissues in ishemic lesion parts.

When administrating the compounds of the present invention as a drug for any of such diseases as described above, the compounds represented by the general formula (1) or the pharmaceutical acceptable salts thereof can be administrated in either their pure form or any forms which are useful as a drug and pharmaceutically accepted for the administration.

For example, the compounds of the present invention and the pharmaceutically acceptable salts can be administrated in an appropriate dosage form which allows prescription with accurate dosages and is easy to administrate orally, transnasally, non-orally, locally, dermally or transrectally, in a dosage form in any of solid, semisolid, lyophilized powder or liquid, such as tablets, suppositories, pills, soft or hard capsules, powders, liquids, suspensions, aerosols and the like.

As the composition of the pharmaceutical dosage forms, customarily-used pharmaceutically acceptable carriers, fillers and the compound represented by the formula (1) of the present invention as either the sole active ingredient or one of the active ingredients are contained, and other drugs, components for formulation use, carriers, adjuvants and the like can be also combined.

The pharmaceutically acceptable composition contains one or more of the compounds represented by the general formula (1) or pharmaceutically acceptable salts thereof in an amount of 1–99% by weight and an appropriate filler for pharmaceutical use in an amount of 99–1% by weight depending upon desired application modes. Preferably, the composition contains one or more compounds of the formula (1) and/or the pharmaceutically acceptable salts in an amount ranging from 5 to 75% by weight and appropriate fillers for pharmaceutical use in an amount for the rest.

The preferable route for administration for the pharmaceutically acceptable composition is oral and simplified standard dose for administration per day for the composition, which is determined and adjusted basing upon the degree of hyperlipemia to be treated, is applied. Such pharmaceutical composition for oral administration use is prepared with one or more compounds of the formula (1) and/or the pharmaceutically acceptable salts thereof and by adding arbitrary commonly-used fillers, such as mannitol, milk sugar, starch, gelatinized starch, magnesium stearate, saccharin sodium, talc, cellulose ether derivatives, glucose, gelatin, sucrose, citrates and propyl gallate, all of those which are pharmaceutical use.

The pharmaceutical compositions prepared as described above are applied in any forms of liquid, suspension, tablet, pill, capsule, powder, repository effusing preparation, suppository or the like.

For such pharmaceutical compositions, it is also capable and useful to add a diluent, such as milk sugar, sucrose and calcium phosphate, a disintegrator, such as sodium chroscarmerose and its derivatives, a lubricant, such as magnesium stearate, a binding agent, such as starch, acacia, polyvinylpyrrolidone, gelatin and cellulose ether derivatives, to the compositions.

In case of suppositories, it is preferable to disperse the compound of the formula (1) or the pharmaceutically acceptable salt thereof into a carrier gradually dissolvable in human body, such as polyoxyethylene glycol or polyethylene glycol (PEG), for examples, PEG1000 (96%) or PEG4000 (4%), to prepare the formulation.

The pharmaceutically acceptable composition in liquid preparation according to the present invention can be prepared into solution or suspension form by either dissolving or suspending one or more compounds of the formula (1) or the pharmaceutically acceptable salts thereof in an amount of 0.5 to 50% by weight and arbitrary pharmaceutically-usable adjuvant in a carrier, such as water, saline solution, aqueous dextrose solution, glycerol and ethanol.

To the pharmaceutical composition according to the present invention, it is also useful to add a small amount of assisting elements, such as humectants, emulsifiers, pH buffer agents and antioxidants, for examples, citric acid, sorbitan monolaurate, triethanolamine oleate, butylated hydroxytoluene and the like, if required.

These pharmaceutical preparations are prepared according to any commonly-known method, for example, a method taught in Remington's Pharmaceutical Sciences, vol. 18, Mack Publishing Company, Easton, Pa., 1990, etc.

One or more compounds represented by the general formula (1) and the pharmaceutically acceptable salts thereof are administrated at their effective doses, respectively, which may be varied depending upon the personal condition and the pathological state of hyperlipemia patients. Normally, the effective dose per 1 KG body weight per day of the compound of the formula (1) is from approximately 0.14 to approximately 14.3 mg/kg/day, and preferably from approximately 0.7 to approximately 10 mg/kg/day, and more preferably from approximately 1.4 to approximately 7.2 mg/kg/day.

For example, when administrating to a human having the body weight of 70 kg, the appropriate dose per day of the compound of the formula (1) and the pharmaceutically acceptable salt thereof may be in a range of from approximately 10 mg to approximately 1.0 g, and preferably from approximately 50 mg to approximately 700 mg, and more preferably from approximately 100 mg to approximately 500 mg.

Now, the representative compounds according to the present invention are presented in Tables 1 and 2. Abbreviations and marks in the tables represent the following means.

Me: methyl, Et: ethyl, Bu: butyl, Ph: phenyl
a1: 1-imidazole, a2:1H-pyrazol-5-yl,
a3: 1H-pyrazol-4-yl,
a4: 1-methylpyrazol-5-yl,
a5: 1-methylpyrazol-3-yl, a6: benzylpyrazol-4-yl,
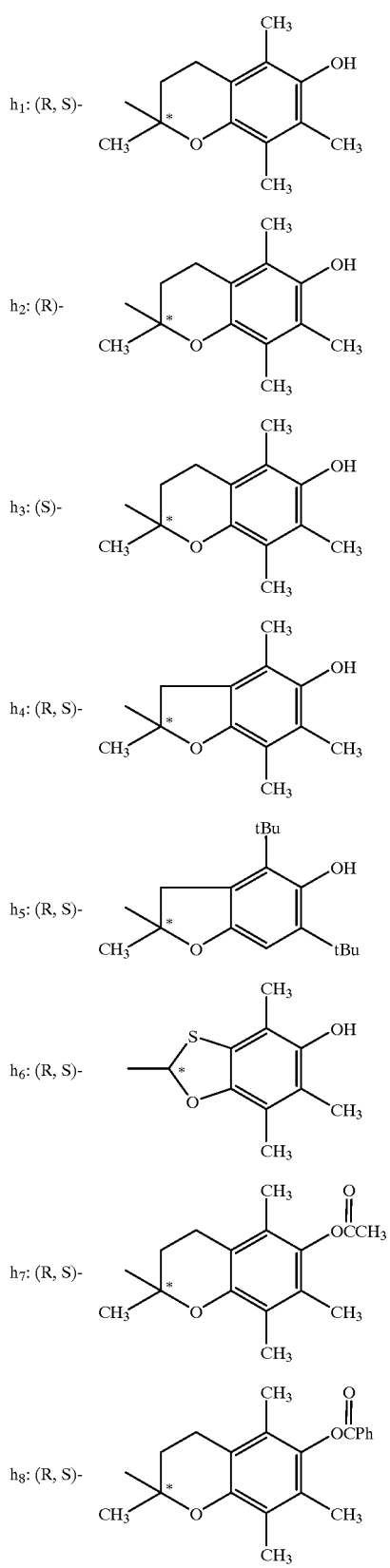
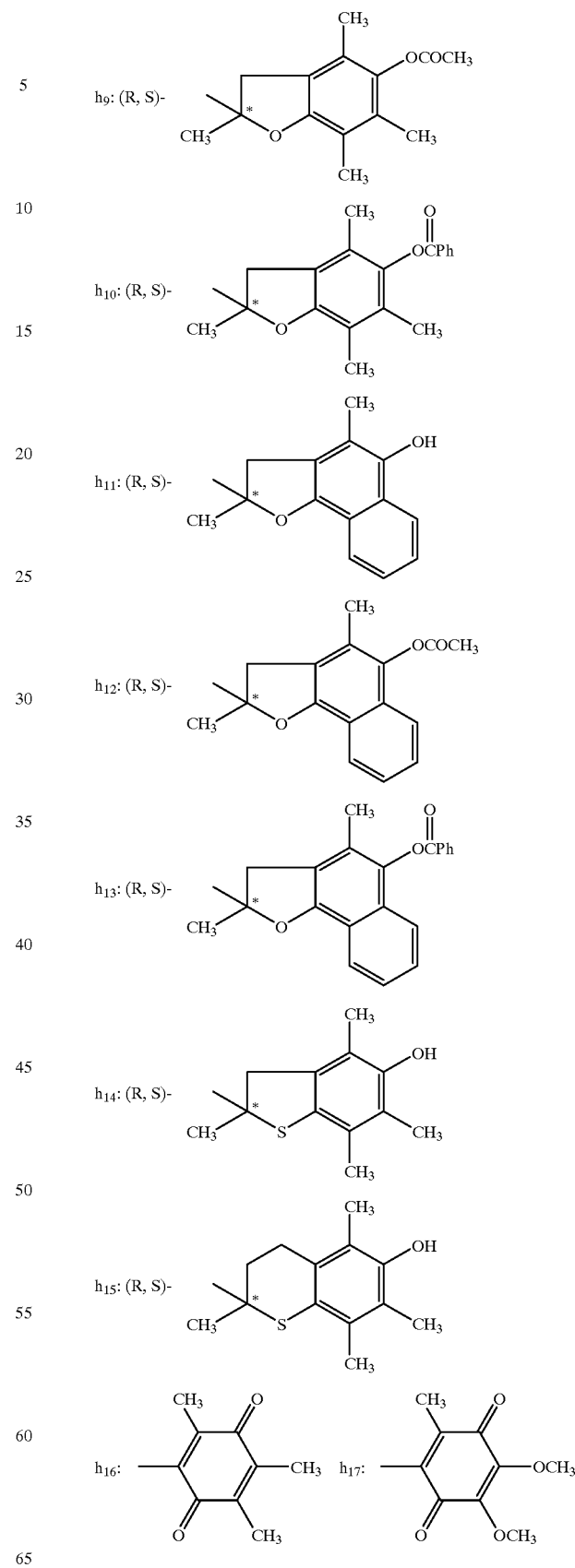

-continued
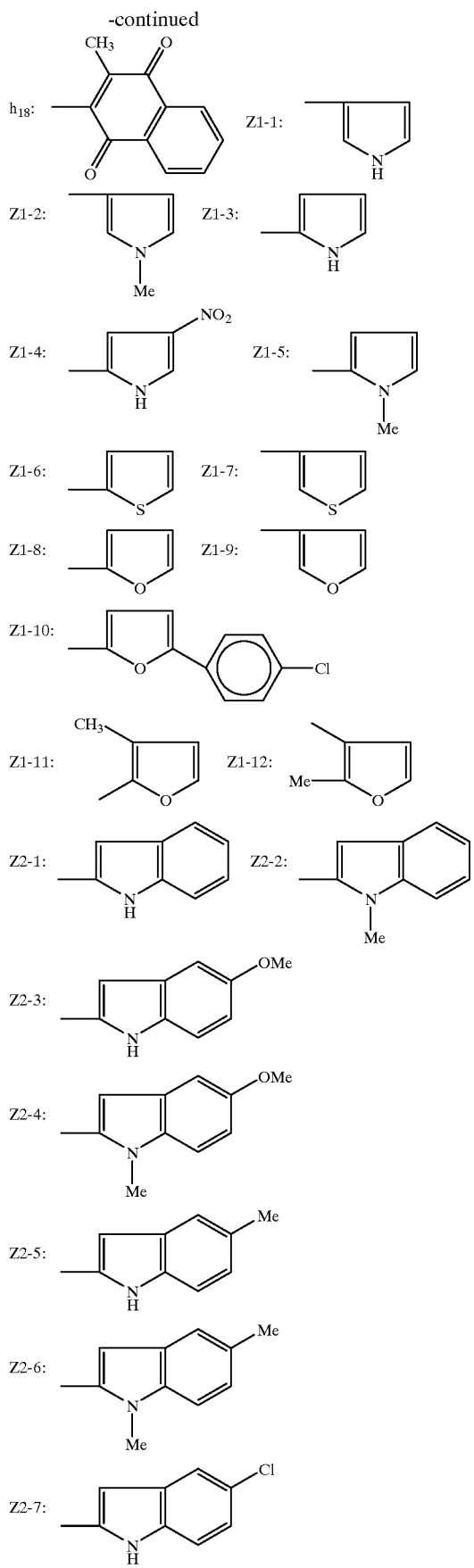
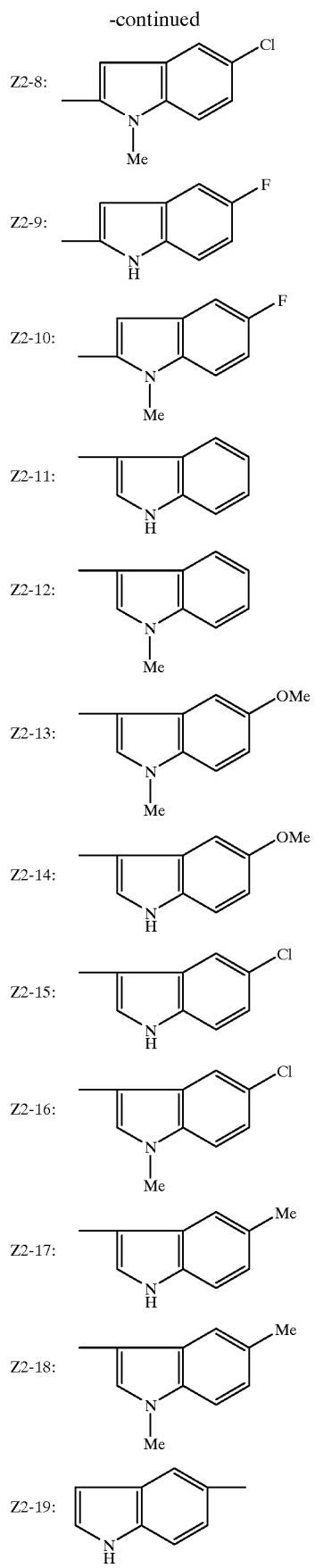

-continued
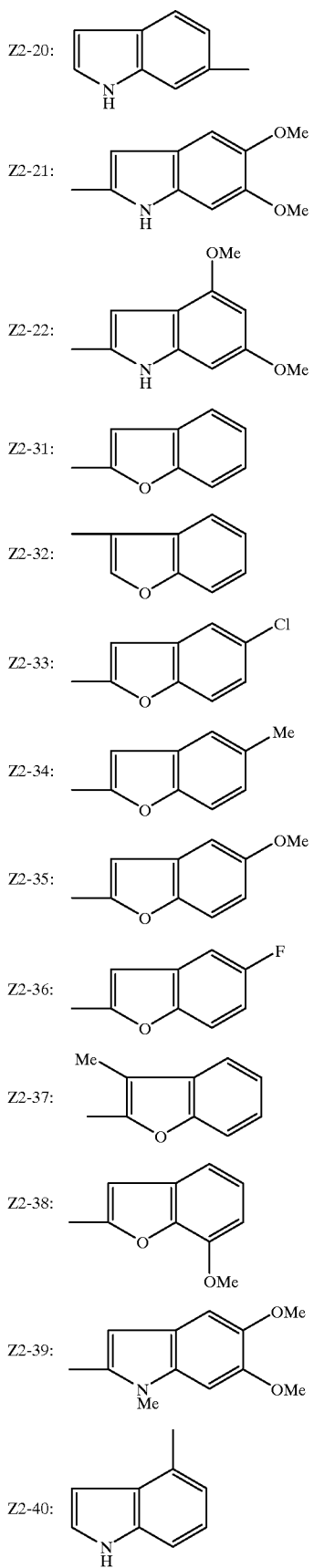
-continued
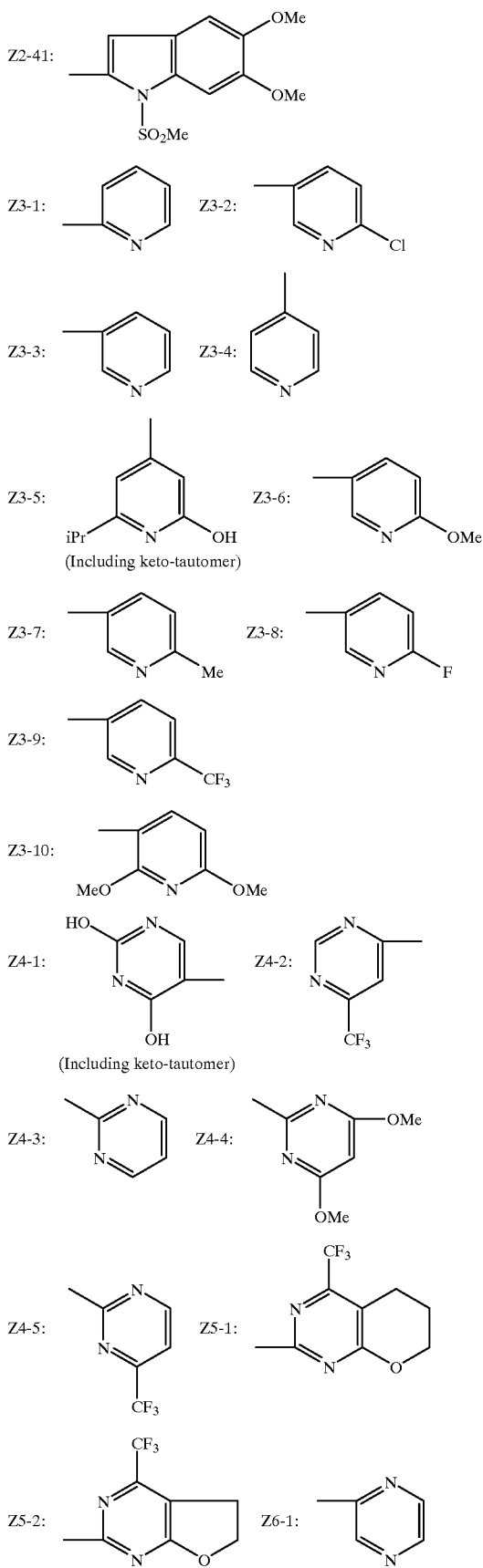

-continued
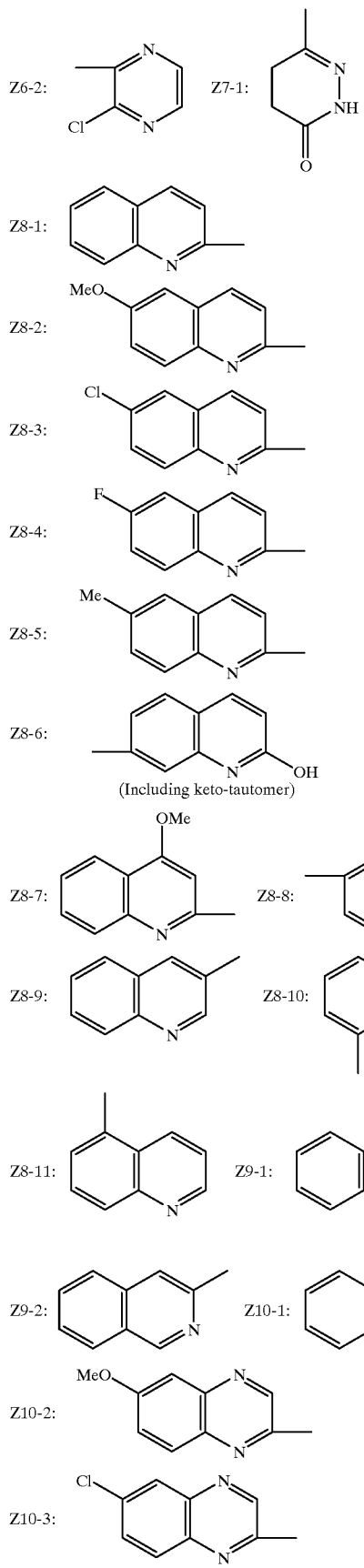
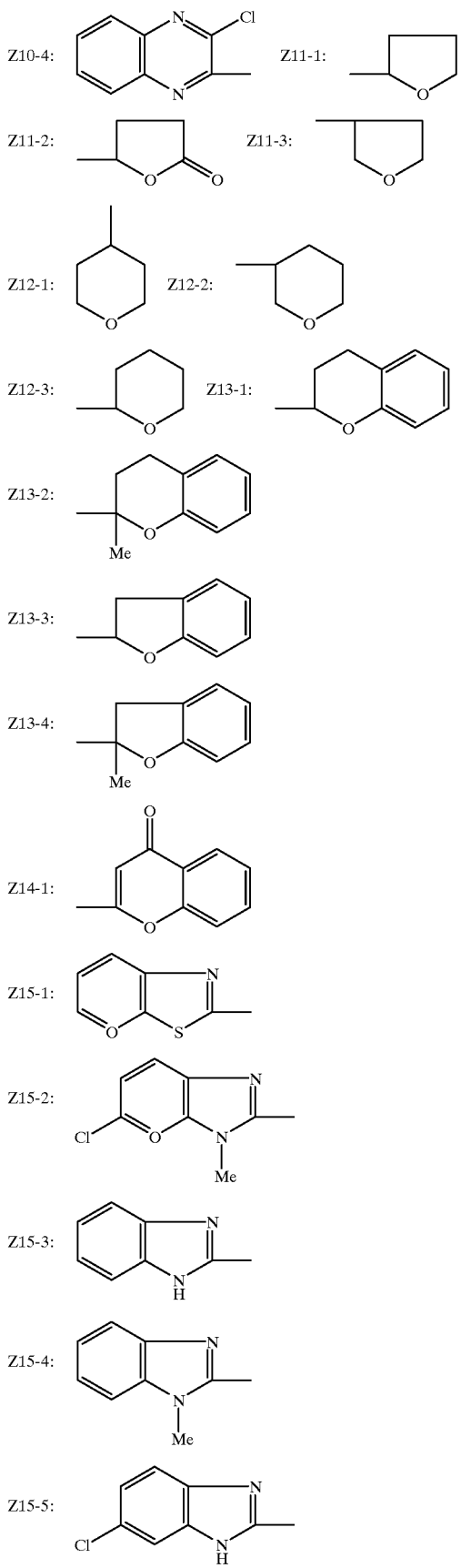

-continued
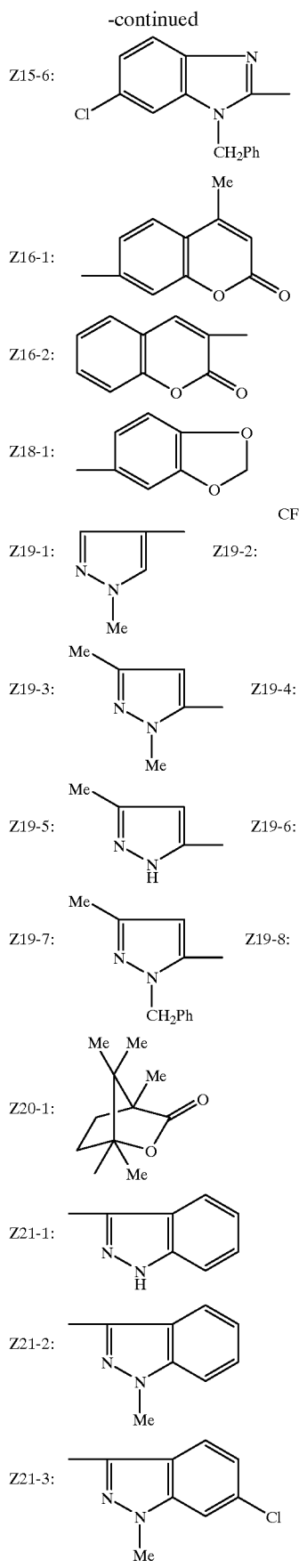
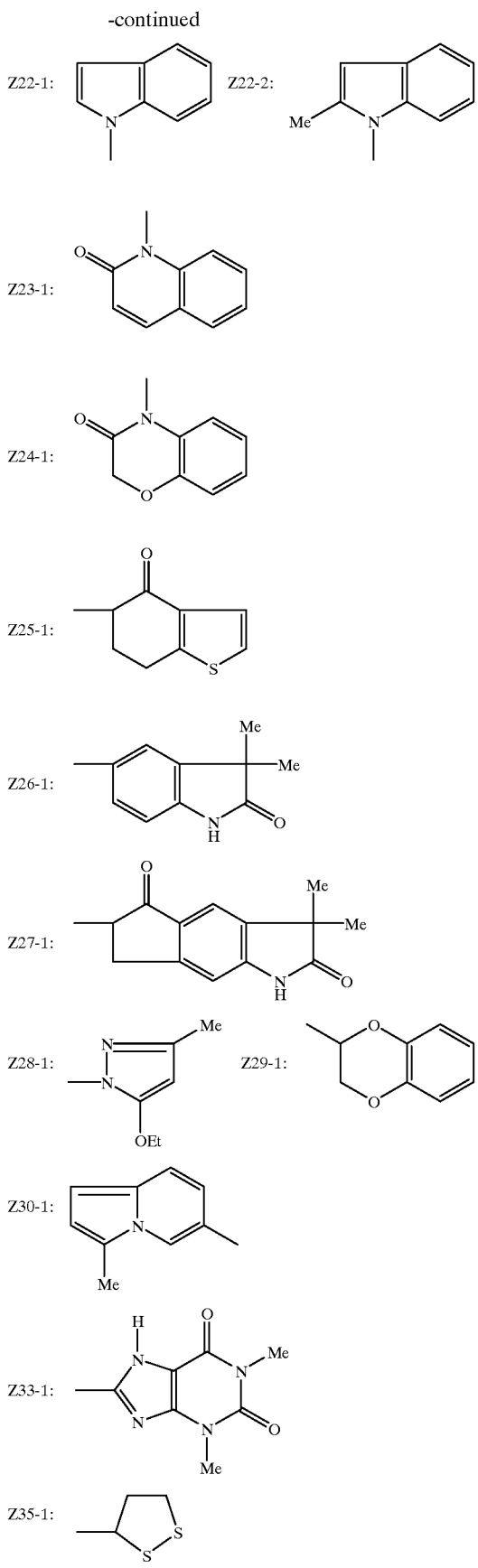

TABLE 1
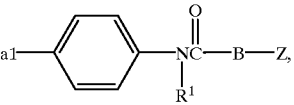 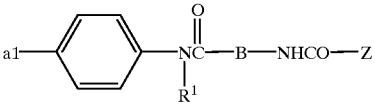
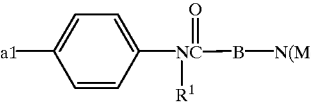 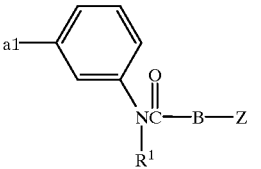
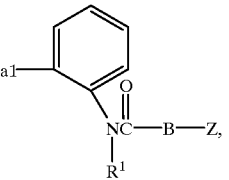 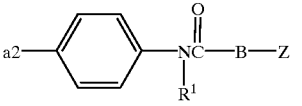
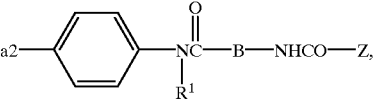 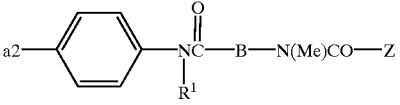
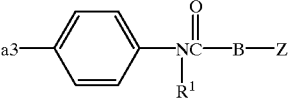 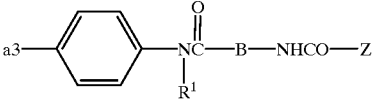
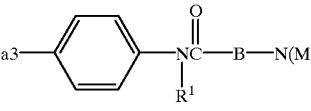 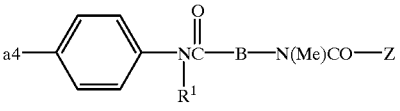
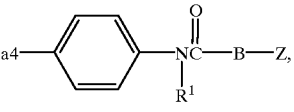 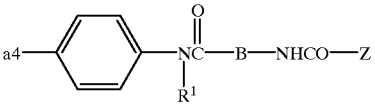
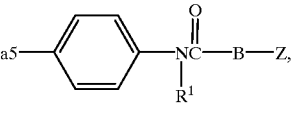 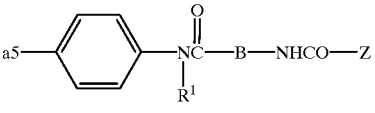
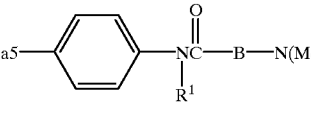 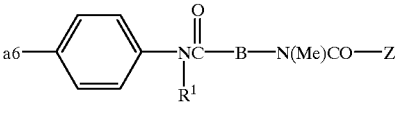
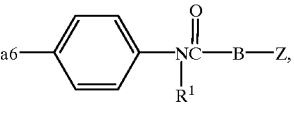 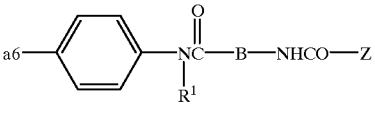
| $R^1$ | B | Z |
|---|---|---|
| H | — | $h_1$ |
| Me | — | $h_1$ |
| H | —$CH_2$— | $h_1$ |
| Me | —$CH_2$— | $h_1$ |
| H | —$(CH_2)_2$— | $h_1$ |
| Me | —$(CH_2)_2$— | $h_1$ |

TABLE 1-continued

| | | |
|---|---|---|
| H | —(CH$_2$)$_3$— | h$_1$ |
| Me | —(CH$_2$)$_3$— | h$_1$ |
| H | —(CH$_2$)$_4$— | h$_1$ |
| Me | —(CH$_2$)$_4$— | h$_1$ |
| H | —(CH$_2$)$_5$— | h$_1$ |
| Me | —(CH$_2$)$_5$— | h$_1$ |
| H | —CH=CH— | h$_1$ |
| Me | —CH=CH— | h$_1$ |
| H | —CH=CH—CH=CH | h$_1$ |
| Me | —CH=CH—CH=CH | h$_1$ |
| H | —CH(Me)CH$_2$— | h$_1$ |
| Me | —CH(Me)CH$_2$— | h$_1$ |
| H | (CH$_2$)$_2$CH(Ph) | h$_1$ |
| Me | (CH$_2$)$_2$CH(Ph) | h$_1$ |
| H | — | h$_2$ |
| Me | — | h$_2$ |
| H | —CH$_2$— | h$_2$ |
| Me | —CH$_2$— | h$_2$ |
| H | —(CH$_2$)$_2$— | h$_2$ |
| Me | —(CH$_2$)$_2$— | h$_2$ |
| H | —(CH$_2$)$_3$— | h$_2$ |
| Me | —(CH$_2$)$_3$— | h$_2$ |
| H | —(CH$_2$)$_4$— | h$_2$ |
| Me | —(CH$_2$)$_4$— | h$_2$ |
| H | —(CH$_2$)$_5$— | h$_2$ |
| Me | —(CH$_2$)$_5$— | h$_2$ |
| H | —CH=CH— | h$_2$ |
| Me | —CH=CH— | h$_2$ |
| H | —CH=CH—CH=CH | h$_2$ |
| Me | —CH=CH—CH=CH | h$_2$ |
| H | —CH(Me)CH$_2$— | h$_2$ |
| Me | —CH(Me)CH$_2$— | h$_2$ |
| H | (CH$_2$)$_2$CH(Ph) | h$_2$ |
| Me | (CH$_2$)$_2$CH(Ph) | h$_2$ |
| H | — | h$_3$ |
| Me | — | h$_3$ |
| H | —CH$_2$— | h$_3$ |
| Me | —CH$_2$— | h$_3$ |
| H | —(CH$_2$)$_2$— | h$_3$ |
| Me | —(CH$_2$)$_2$— | h$_3$ |
| H | —(CH$_2$)$_3$— | h$_3$ |
| Me | —(CH$_2$)$_3$— | h$_3$ |
| H | —(CH$_2$)$_4$— | h$_3$ |
| Me | —(CH$_2$)$_4$— | h$_3$ |
| H | —(CH$_2$)$_5$— | h$_3$ |
| Me | —(CH$_2$)$_5$— | h$_3$ |
| H | —CH=CH— | h$_3$ |
| Me | —CH=CH— | h$_3$ |
| H | —CH=CH—CH=CH | h$_3$ |
| Me | —CH=CH—CH=CH | h$_3$ |
| H | —CH(Me)CH$_2$— | h$_3$ |
| Me | —CH(Me)CH$_2$— | h$_3$ |
| H | (CH$_2$)$_2$CH(Ph) | h$_3$ |
| Me | (CH$_2$)$_2$CH(Ph) | h$_3$ |
| H | — | h$_4$ |
| Me | — | h$_4$ |
| H | —CH$_2$— | h$_4$ |
| Me | —CH$_2$— | h$_4$ |
| H | —(CH$_2$)$_2$— | h$_4$ |
| Me | —(CH$_2$)$_2$— | h$_4$ |
| H | —(CH$_2$)$_3$— | h$_4$ |
| Me | —(CH$_2$)$_3$— | h$_4$ |
| H | —(CH$_2$)$_4$— | h$_4$ |
| Me | —(CH$_2$)$_4$— | h$_4$ |
| H | —(CH$_2$)$_5$— | h$_4$ |
| Me | —(CH$_2$)$_5$— | h$_4$ |
| H | —CH=CH— | h$_4$ |
| Me | —CH=CH— | h$_4$ |
| H | —CH=CH—CH=CH | h$_4$ |
| Me | —CH=CH—CH=CH | h$_4$ |
| H | —CH(Me)CH$_2$— | h$_4$ |
| Me | —CH(Me)CH$_2$— | h$_4$ |
| H | (CH$_2$)$_2$CH(Ph) | h$_4$ |
| Me | (CH$_2$)$_2$CH(Ph) | h$_4$ |
| H | — | h$_5$ |
| Me | — | h$_5$ |
| H | —CH$_2$— | h$_5$ |
| Me | —CH$_2$— | h$_5$ |
| H | —(CH$_2$)$_2$— | h$_5$ |

TABLE 1-continued

| | | |
|---|---|---|
| Me | —(CH$_2$)$_2$— | h$_5$ |
| H | —(CH$_2$)$_3$— | h$_5$ |
| Me | —(CH$_2$)$_3$— | h$_5$ |
| H | —(CH$_2$)$_4$— | h$_5$ |
| Me | —(CH$_2$)$_4$— | h$_5$ |
| H | —(CH$_2$)$_5$— | h$_5$ |
| Me | —(CH$_2$)$_5$— | h$_5$ |
| H | —CH=CH— | h$_5$ |
| Me | —CH=CH— | h$_5$ |
| H | —CH=CH—CH=CH | h$_5$ |
| Me | —CH=CH—CH=CH | h$_5$ |
| H | —CH(Me)CH$_2$— | h$_5$ |
| Me | —CH(Me)CH$_2$— | h$_5$ |
| H | (CH$_2$)$_2$CH(Ph) | h$_5$ |
| Me | (CH$_2$)$_2$CH(Ph) | h$_5$ |
| H | — | h$_6$ |
| Me | — | h$_6$ |
| H | —CH$_2$— | h$_6$ |
| Me | —CH$_2$— | h$_6$ |
| H | —(CH$_2$)$_2$— | h$_6$ |
| Me | —(CH$_2$)$_2$— | h$_6$ |
| H | —(CH$_2$)$_3$— | h$_6$ |
| Me | —(CH$_2$)$_3$— | h$_6$ |
| H | —(CH$_2$)$_4$— | h$_6$ |
| Me | —(CH$_2$)$_4$— | h$_6$ |
| H | —(CH$_2$)$_5$— | h$_6$ |
| Me | —(CH$_2$)$_5$— | h$_6$ |
| H | —CH=CH— | h$_6$ |
| Me | —CH=CH— | h$_6$ |
| H | —CH=CH—CH=CH | h$_6$ |
| Me | —CH=CH—CH=CH | h$_6$ |
| H | —CH(Me)CH$_2$— | h$_6$ |
| Me | —CH(Me)CH$_2$— | h$_6$ |
| H | (CH$_2$)$_2$CH(Ph) | h$_6$ |
| Me | (CH$_2$)$_2$CH(Ph) | h$_6$ |
| H | — | h$_7$ |
| Me | — | h$_7$ |
| H | —CH$_2$— | h$_7$ |
| Me | —CH$_2$— | h$_7$ |
| H | —(CH$_2$)$_2$— | h$_7$ |
| Me | —(CH$_2$)$_2$— | h$_7$ |
| H | —(CH$_2$)$_3$— | h$_7$ |
| Me | —(CH$_2$)$_3$— | h$_7$ |
| H | —(CH$_2$)$_4$— | h$_7$ |
| Me | —(CH$_2$)$_4$— | h$_7$ |
| H | —(CH$_2$)$_5$— | h$_7$ |
| Me | —(CH$_2$)$_5$— | h$_7$ |
| H | —CH=CH— | h$_7$ |
| Me | —CH=CH— | h$_7$ |
| H | —CH=CH—CH=CH | h$_7$ |
| Me | —CH=CH—CH=CH | h$_7$ |
| H | —CH(Me)CH$_2$— | h$_7$ |
| Me | —CH(Me)CH$_2$— | h$_7$ |
| H | (CH$_2$)$_2$CH(Ph) | h$_7$ |
| Me | (CH$_2$)$_2$CH(Ph) | h$_7$ |
| H | — | h$_8$ |
| Me | — | h$_8$ |
| H | —CH$_2$— | h$_8$ |
| Me | —CH$_2$— | h$_8$ |
| H | —(CH$_2$)$_2$— | h$_8$ |
| Me | —(CH$_2$)$_2$— | h$_8$ |
| H | —(CH$_2$)$_3$— | h$_8$ |
| Me | —(CH$_2$)$_3$— | h$_8$ |
| H | —(CH$_2$)$_4$— | h$_8$ |
| Me | —(CH$_2$)$_4$— | h$_8$ |
| H | —(CH$_2$)$_5$— | h$_8$ |
| Me | —(CH$_2$)$_5$— | h$_8$ |
| H | —CH=CH— | h$_8$ |
| Me | —CH=CH— | h$_8$ |
| H | —CH=CH—CH=CH | h$_8$ |
| Me | —CH=CH—CH=CH | h$_8$ |
| H | —CH(Me)CH$_2$— | h$_8$ |
| Me | —CH(Me)CH$_2$— | h$_8$ |
| H | (CH$_2$)$_2$CH(Ph) | h$_8$ |
| Me | (CH$_2$)$_2$CH(Ph) | h$_8$ |
| H | — | h$_9$ |
| Me | — | h$_9$ |
| H | —CH$_2$— | h$_9$ |
| Me | —CH$_2$— | h$_9$ |

TABLE 1-continued

| | | |
|---|---|---|
| H | —(CH$_2$)$_2$— | h$_9$ |
| Me | —(CH$_2$)$_2$— | h$_9$ |
| H | —(CH$_2$)$_3$— | h$_9$ |
| Me | —(CH$_2$)$_3$— | h$_9$ |
| H | —(CH$_2$)$_4$— | h$_9$ |
| Me | —(CH$_2$)$_4$— | h$_9$ |
| H | —(CH$_2$)$_5$— | h$_9$ |
| Me | —(CH$_2$)$_5$— | h$_9$ |
| H | —CH=CH— | h$_9$ |
| Me | —CH=CH— | h$_9$ |
| H | —CH=CH—CH=CH | h$_9$ |
| Me | —CH=CH—CH=CH | h$_9$ |
| H | —CH(Me)CH$_2$— | h$_9$ |
| Me | —CH(Me)CH$_2$— | h$_9$ |
| H | (CH$_2$)$_2$CH(Ph) | h$_9$ |
| Me | (CH$_2$)$_2$CH(Ph) | h$_9$ |
| H | — | h$_{10}$ |
| Me | — | h$_{10}$ |
| H | — | h$_{10}$ |
| Me | — | h$_{10}$ |
| H | —CH$_2$— | h$_{10}$ |
| Me | —CH$_2$— | h$_{10}$ |
| H | —(CH$_2$)$_3$— | h$_{10}$ |
| Me | —(CH$_2$)$_3$— | h$_{10}$ |
| H | —(CH$_2$)$_4$— | h$_{10}$ |
| Me | —(CH$_2$)$_4$— | h$_{10}$ |
| H | —(CH$_2$)$_5$— | h$_{10}$ |
| Me | —(CH$_2$)$_5$— | h$_{10}$ |
| H | —CH=CH— | h$_{10}$ |
| Me | —CH=CH— | h$_{10}$ |
| H | —CH=CH—CH=CH | h$_{10}$ |
| Me | —CH=CH—CH=CH | h$_{10}$ |
| H | —CH(Me)CH$_2$— | h$_{10}$ |
| Me | —CH(Me)CH$_2$— | h$_{10}$ |
| H | (CH$_2$)$_2$CH(Ph) | h$_{10}$ |
| Me | (CH$_2$)$_2$CH(Ph) | h$_{10}$ |
| H | — | h$_{11}$ |
| Me | — | h$_{11}$ |
| H | —CH$_2$— | h$_{11}$ |
| Me | —CH$_2$— | h$_{11}$ |
| H | —(CH$_2$)$_2$— | h$_{11}$ |
| Me | —(CH$_2$)$_2$— | h$_{11}$ |
| H | —(CH$_2$)$_3$— | h$_{11}$ |
| Me | —(CH$_2$)$_3$— | h$_{11}$ |
| H | —(CH$_2$)$_4$— | h$_{11}$ |
| Me | —(CH$_2$)$_4$— | h$_{11}$ |
| H | —(CH$_2$)$_5$— | h$_{11}$ |
| Me | —(CH$_2$)$_5$— | h$_{11}$ |
| H | —CH=CH— | h$_{11}$ |
| Me | —CH=CH— | h$_{11}$ |
| H | —CH=CH—CH=CH | h$_{11}$ |
| Me | —CH=CH—CH=CH | h$_{11}$ |
| H | —CH(Me)CH$_2$— | h$_{11}$ |
| Me | —CH(Me)CH$_2$— | h$_{11}$ |
| H | (CH$_2$)$_2$CH(Ph) | h$_{11}$ |
| Me | (CH$_2$)$_2$CH(Ph) | h$_{11}$ |
| H | — | h$_{12}$ |
| Me | — | h$_{12}$ |
| H | —CH$_2$— | h$_{12}$ |
| Me | —CH$_2$— | h$_{12}$ |
| H | —(CH$_2$)$_2$— | h$_{12}$ |
| Me | —(CH$_2$)$_2$— | h$_{12}$ |
| H | —(CH$_2$)$_3$— | h$_{12}$ |
| Me | —(CH$_2$)$_3$— | h$_{12}$ |
| H | —(CH$_2$)$_4$— | h$_{12}$ |
| Me | —(CH$_2$)$_4$— | h$_{12}$ |
| H | —(CH$_2$)$_5$— | h$_{12}$ |
| Me | —(CH$_2$)$_5$— | h$_{12}$ |
| H | —CH=CH— | h$_{12}$ |
| Me | —CH=CH— | h$_{12}$ |
| H | —CH=CH—CH=CH | h$_{12}$ |
| Me | —CH=CH—CH=CH | h$_{12}$ |
| H | —CH(Me)CH$_2$— | h$_{12}$ |
| Me | —CH(Me)CH$_2$— | h$_{12}$ |
| H | (CH$_2$)$_2$CH(Ph) | h$_{12}$ |
| Me | (CH$_2$)$_2$CH(Ph) | h$_{12}$ |
| H | — | h$_{13}$ |
| Me | — | h$_{13}$ |
| H | —CH$_2$— | h$_{13}$ |

TABLE 1-continued

| | | |
|---|---|---|
| Me | —CH$_2$— | h$_{13}$ |
| H | —(CH$_2$)$_2$— | h$_{13}$ |
| Me | —(CH$_2$)$_2$— | h$_{13}$ |
| H | —(CH$_2$)$_3$— | h$_{13}$ |
| Me | —(CH$_2$)$_3$— | h$_{13}$ |
| H | —(CH$_2$)$_4$— | h$_{13}$ |
| Me | —(CH$_2$)$_4$— | h$_{13}$ |
| H | —(CH$_2$)$_5$— | h$_{13}$ |
| Me | —(CH$_2$)$_5$— | h$_{13}$ |
| H | —CH=CH— | h$_{13}$ |
| Me | —CH=CH— | h$_{13}$ |
| H | —CH=CH—CH=CH | h$_{13}$ |
| Me | —CH=CH—CH=CH | h$_{13}$ |
| H | —CH(Me)CH$_2$— | h$_{13}$ |
| Me | —CH(Me)CH$_2$— | h$_{13}$ |
| H | (CH$_2$)$_2$CH(Ph) | h$_{13}$ |
| Me | (CH$_2$)$_2$CH(Ph) | h$_{13}$ |
| H | — | h$_{14}$ |
| Me | — | h$_{14}$ |
| H | —CH$_2$— | h$_{14}$ |
| Me | —CH$_2$— | h$_{14}$ |
| H | —(CH$_2$)$_2$— | h$_{14}$ |
| Me | —(CH$_2$)$_2$— | h$_{14}$ |
| H | —(CH$_2$)$_3$— | h$_{14}$ |
| Me | —(CH$_2$)$_3$— | h$_{14}$ |
| H | —(CH$_2$)$_4$— | h$_{14}$ |
| Me | —(CH$_2$)$_4$— | h$_{14}$ |
| H | —(CH$_2$)$_5$— | h$_{14}$ |
| Me | —(CH$_2$)$_5$— | h$_{14}$ |
| H | —CH=CH— | h$_{14}$ |
| Me | —CH=CH— | h$_{14}$ |
| H | —CH=CH—CH=CH | h$_{14}$ |
| Me | —CH=CH—CH=CH | h$_{14}$ |
| H | — | h$_{15}$ |
| Me | — | h$_{15}$ |
| H | —CH$_2$— | h$_{15}$ |
| Me | —CH$_2$— | h$_{15}$ |
| H | —(CH$_2$)$_2$— | h$_{15}$ |
| Me | —(CH$_2$)$_2$— | h$_{15}$ |
| H | —(CH$_2$)$_3$— | h$_{15}$ |
| Me | —(CH$_2$)$_3$— | h$_{15}$ |
| H | —(CH$_2$)$_4$— | h$_{15}$ |
| Me | —(CH$_2$)$_4$— | h$_{15}$ |
| H | —(CH$_2$)$_5$— | h$_{15}$ |
| Me | —(CH$_2$)$_5$— | h$_{15}$ |
| H | —CH=CH— | h$_{15}$ |
| Me | —CH=CH— | h$_{15}$ |
| H | —CH=CH—CH=CH | h$_{15}$ |
| Me | —CH=CH—CH=CH | h$_{15}$ |
| H | (CH$_2$)$_2$CH(Ph) | h$_{15}$ |
| H | —CH(Me)CH$_2$— | h$_{15}$ |
| H | — | h$_{16}$ |
| Me | — | h$_{16}$ |
| H | —CH$_2$— | h$_{16}$ |
| Me | —CH$_2$— | h$_{16}$ |
| H | —(CH$_2$)$_2$— | h$_{16}$ |
| Me | —(CH$_2$)$_2$— | h$_{16}$ |
| H | —(CH$_2$)$_3$— | h$_{16}$ |
| Me | —(CH$_2$)$_3$— | h$_{16}$ |
| H | —(CH$_2$)$_4$— | h$_{16}$ |
| Me | —(CH$_2$)$_4$— | h$_{16}$ |
| H | —(CH$_2$)$_5$— | h$_{16}$ |
| Me | —(CH$_2$)$_5$— | h$_{16}$ |
| H | —CH=CH— | h$_{16}$ |
| Me | —CH=CH— | h$_{16}$ |
| H | —CH=CH—CH=CH | h$_{16}$ |
| Me | —CH=CH—CH=CH | h$_{16}$ |
| H | (CH$_2$)$_2$CH(Ph) | h$_{16}$ |
| H | —CH(Me)CH$_2$— | h$_{16}$ |
| H | — | h$_{17}$ |
| Me | — | h$_{17}$ |
| H | —CH$_2$— | h$_{17}$ |
| Me | —CH$_2$— | h$_{17}$ |
| H | —(CH$_2$)$_2$— | h$_{17}$ |
| Me | —(CH$_2$)$_2$— | h$_{17}$ |
| H | —(CH$_2$)$_3$— | h$_{17}$ |
| Me | —(CH$_2$)$_3$— | h$_{17}$ |
| H | —(CH$_2$)$_4$— | h$_{17}$ |
| Me | —(CH$_2$)$_4$— | h$_{17}$ |

TABLE 1-continued

| | | |
|---|---|---|
| H | —(CH$_2$)$_5$— | h$_{17}$ |
| Me | —(CH$_2$)$_5$— | h$_{17}$ |
| H | —CH=CH— | h$_{17}$ |
| Me | —CH=CH— | h$_{17}$ |
| H | —CH=CH—CH=CH | h$_{17}$ |
| Me | —CH=CH—CH=CH | h$_{17}$ |
| H | — | h$_{18}$ |
| Me | — | h$_{18}$ |
| H | —CH$_2$— | h$_{18}$ |
| Me | —CH$_2$— | h$_{18}$ |
| H | —(CH$_2$)$_2$— | h$_{18}$ |
| Me | —(CH$_2$)$_2$— | h$_{18}$ |
| H | —(CH$_2$)$_3$— | h$_{18}$ |
| Me | —(CH$_2$)$_3$— | h$_{18}$ |
| H | —(CH$_2$)$_4$— | h$_{18}$ |
| Me | —(CH$_2$)$_4$— | h$_{18}$ |
| H | —(CH$_2$)$_5$— | h$_{18}$ |
| Me | —(CH$_2$)$_5$— | h$_{18}$ |
| H | —CH=CH— | h$_{18}$ |
| Me | —CH=CH— | h$_{18}$ |
| H | —CH=CH—CH=CH | h$_{18}$ |
| Me | —CH=CH—CH=CH | h$_{18}$ |
| H | (CH$_2$)$_2$CH(Ph) | h$_{18}$ |
| H | —CH(Me)CH$_2$— | h$_{18}$ |
| H | — | h$_{19}$ |
| Me | — | h$_{19}$ |
| H | —CH$_2$— | h$_{19}$ |
| Me | —CH$_2$— | h$_{19}$ |
| H | —(CH$_2$)$_2$— | h$_{19}$ |
| Me | —(CH$_2$)$_2$— | h$_{19}$ |
| H | —(CH$_2$)$_3$— | h$_{19}$ |
| Me | —(CH$_2$)$_3$— | h$_{19}$ |
| H | —(CH$_2$)$_4$— | h$_{19}$ |
| Me | —(CH$_2$)$_4$— | h$_{19}$ |
| H | —(CH$_2$)$_5$— | h$_{19}$ |
| Me | —(CH$_2$)$_5$— | h$_{19}$ |
| H | —CH=CH— | h$_{19}$ |
| Me | —CH=CH— | h$_{19}$ |
| H | —CH=CH—CH=CH | h$_{19}$ |
| Me | —CH=CH—CH=CH | h$_{19}$ |
| H | (CH$_2$)$_2$CH(Ph) | h$_{19}$ |
| H | —CH(Me)CH$_2$— | h$_{19}$ |

TABLE 2

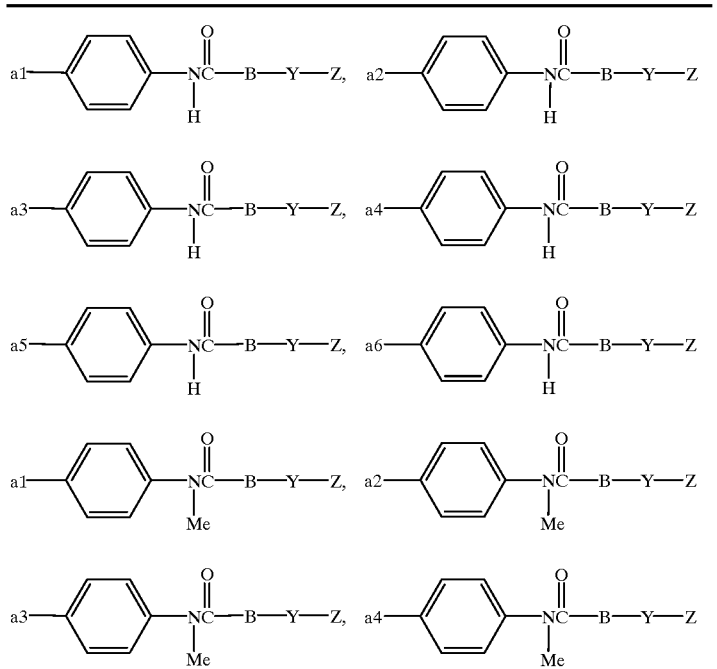

TABLE 2-continued
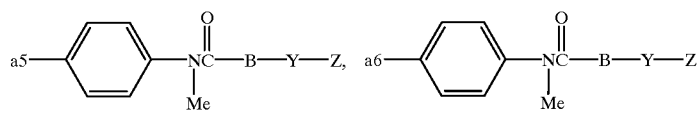
| TABLE 2-1 |
|---|
| Compounds of which B and Y are single bonding. |
| Z |
| Z1-1 |
| Z1-2 |
| Z1-3 |
| Z1-4 |
| Z1-5 |
| Z1-6 |
| Z1-7 |
| Z1-8 |
| Z1-9 |
| Z1-10 |
| Z1-11 |
| Z1-12 |
| Z2-1 |
| Z2-2 |
| Z2-3 |
| Z2-4 |
| Z2-5 |
| Z2-6 |
| Z2-7 |
| Z2-8 |
| Z2-9 |
| Z2-10 |
| Z2-11 |
| Z2-12 |
| Z2-13 |
| Z2-14 |
| Z2-15 |
| Z2-16 |
| Z2-17 |
| Z2-18 |
| Z2-19 |
| Z2-20 |
| Z2-21 |
| Z2-22 |
| Z2-23 |
| Z2-24 |
| Z2-25 |
| Z2-26 |
| Z2-27 |
| Z2-28 |
| Z2-29 |
| Z2-30 |
| Z2-31 |
| Z2-32 |
| Z2-33 |
| Z2-34 |
| Z2-35 |
| Z2-36 |
| Z2-37 |
| Z2-38 |
| Z2-39 |
| Z2-40 |
| Z2-41 |
| Z3-1 |
| Z3-2 |
| Z3-3 |
| Z3-4 |
| Z3-5 |
| Z3-6 |
| Z3-7 |
| Z3-8 |
| Z3-9 |
| TABLE 2-1-continued |
|---|
| Compounds of which B and Y are single bonding. |
| Z |
| Z3-10 |
| Z4-1 |
| Z4-2 |
| Z4-3 |
| Z4-4 |
| Z4-5 |
| Z5-1 |
| Z5-2 |
| Z6-1 |
| Z6-2 |
| Z7-1 |
| Z8-1 |
| Z8-2 |
| Z8-3 |
| Z8-4 |
| Z8-5 |
| Z8-6 |
| Z8-7 |
| Z8-8 |
| Z8-9 |
| Z8-10 |
| Z8-11 |
| Z9-1 |
| Z9-2 |
| Z10-1 |
| Z10-2 |
| Z10-3 |
| Z10-4 |
| Z11-1 |
| Z11-2 |
| Z11-3 |
| Z12-1 |
| Z12-2 |
| Z12-3 |
| Z13-1 |
| Z13-2 |
| Z13-3 |
| Z13-4 |
| Z14-1 |
| Z15-1 |
| Z15-2 |
| Z15-3 |
| Z15-4 |
| Z15-5 |
| Z15-6 |
| Z16-1 |
| Z16-2 |
| Z18-1 |
| Z19-1 |
| Z19-2 |
| Z19-3 |
| Z19-4 |
| Z19-5 |
| Z19-6 |
| Z19-7 |
| Z19-8 |
| Z20-1 |
| Z21-1 |
| Z21-2 |
| Z21-3 |
| Z22-1 |
| Z22-2 |

TABLE 2-1-continued

Compounds of which B and Y are single bonding.

| Z |
|---|
| Z23-1 |
| Z24-1 |
| Z25-1 |
| Z26-1 |
| Z27-1 |
| Z28-1 |
| Z29-1 |
| Z30-1 |
| Z33-1 |
| Z35-1 |

TABLE 2-2

| B | Y | Z |
|---|---|---|
| —CH$_2$— | O | Z1-1 |
| —CH$_2$— | O | Z1-2 |
| —CH$_2$— | O | Z1-3 |
| —CH$_2$— | O | Z1-4 |
| —CH$_2$— | O | Z1-5 |
| —CH$_2$— | O | Z1-6 |
| —CH$_2$— | O | Z1-7 |
| —CH$_2$— | O | Z1-8 |
| —CH$_2$— | O | Z1-9 |
| —CH$_2$— | O | Z1-10 |
| —CH$_2$— | O | Z1-11 |
| —CH$_2$— | O | Z1-12 |
| —CH$_2$— | O | Z2-1 |
| —CH$_2$— | O | Z2-2 |
| —CH$_2$— | O | Z2-3 |
| —CH$_2$— | O | Z2-4 |
| —CH$_2$— | O | Z2-5 |
| —CH$_2$— | O | Z2-6 |
| —CH$_2$— | O | Z2-7 |
| —CH$_2$— | O | Z2-8 |
| —CH$_2$— | O | Z2-9 |
| —CH$_2$— | O | Z2-10 |
| —CH$_2$— | O | Z2-11 |
| —CH$_2$— | O | Z2-12 |
| —CH$_2$— | O | Z2-13 |
| —CH$_2$— | O | Z2-14 |
| —CH$_2$— | O | Z2-15 |
| —CH$_2$— | O | Z2-16 |
| —CH$_2$— | O | Z2-17 |
| —CH$_2$— | O | Z2-18 |
| —CH$_2$— | O | Z2-19 |
| —CH$_2$— | O | Z2-20 |
| —CH$_2$— | O | Z2-21 |
| —CH$_2$— | O | Z2-22 |
| —CH$_2$— | O | Z2-23 |
| —CH$_2$— | O | Z2-24 |
| —CH$_2$— | O | Z2-25 |
| —CH$_2$— | O | Z2-26 |
| —CH$_2$— | O | Z2-27 |
| —CH$_2$— | O | Z2-28 |
| —CH$_2$— | O | Z2-29 |
| —CH$_2$— | O | Z2-30 |
| —CH$_2$— | O | Z2-31 |
| —CH$_2$— | O | Z2-32 |
| —CH$_2$— | O | Z2-33 |
| —CH$_2$— | O | Z2-34 |
| —CH$_2$— | O | Z2-35 |
| —CH$_2$— | O | Z2-36 |
| —CH$_2$— | O | Z2-37 |
| —CH$_2$— | O | Z2-38 |
| —CH$_2$— | O | Z2-39 |
| —CH$_2$— | O | Z2-40 |
| —CH$_2$— | O | Z2-41 |
| —CH$_2$— | O | Z3-1 |
| —CH$_2$— | O | Z3-2 |
| —CH$_2$— | O | Z3-3 |
| —CH$_2$— | O | Z3-4 |

TABLE 2-2-continued

| B | Y | Z |
|---|---|---|
| —CH$_2$— | O | Z3-5 |
| —CH$_2$— | O | Z3-6 |
| —CH$_2$— | O | Z3-7 |
| —CH$_2$— | O | Z3-8 |
| —CH$_2$— | O | Z3-9 |
| —CH$_2$— | O | Z3-10 |
| —CH$_2$— | O | Z4-1 |
| —CH$_2$— | O | Z4-2 |
| —CH$_2$— | O | Z4-3 |
| —CH$_2$— | O | Z4-4 |
| —CH$_2$— | O | Z4-5 |
| —CH$_2$— | O | Z5-1 |
| —CH$_2$— | O | Z5-2 |
| —CH$_2$— | O | Z6-1 |
| —CH$_2$— | O | Z6-2 |
| —CH$_2$— | O | Z7-1 |
| —CH$_2$— | O | Z8-1 |
| —CH$_2$— | O | Z8-2 |
| —CH$_2$— | O | Z8-3 |
| —CH$_2$— | O | Z8-4 |
| —CH$_2$— | O | Z8-5 |
| —CH$_2$— | O | Z8-6 |
| —CH$_2$— | O | Z8-7 |
| —CH$_2$— | O | Z8-8 |
| —CH$_2$— | O | Z8-9 |
| —CH$_2$— | O | Z8-10 |
| —CH$_2$— | O | Z8-11 |
| —CH$_2$— | O | Z9-1 |
| —CH$_2$— | O | Z9-2 |
| —CH$_2$— | O | Z10-1 |
| —CH$_2$— | O | Z10-2 |
| —CH$_2$— | O | Z10-3 |
| —CH$_2$— | O | Z10-4 |
| —CH$_2$— | O | Z11-1 |
| —CH$_2$— | O | Z11-2 |
| —CH$_2$— | O | Z11-3 |
| —CH$_2$— | O | Z12-1 |
| —CH$_2$— | O | Z12-2 |
| —CH$_2$— | O | Z12-3 |
| —CH$_2$— | O | Z13-1 |
| —CH$_2$— | O | Z13-2 |
| —CH$_2$— | O | Z13-3 |
| —CH$_2$— | O | Z13-4 |
| —CH$_2$— | O | Z14-1 |
| —CH$_2$— | O | Z15-1 |
| —CH$_2$— | O | Z15-2 |
| —CH$_2$— | O | Z15-3 |
| —CH$_2$— | O | Z15-4 |
| —CH$_2$— | O | Z15-5 |
| —CH$_2$— | O | Z15-6 |
| —CH$_2$— | O | Z16-1 |
| —CH$_2$— | O | Z16-2 |
| —CH$_2$— | O | Z18-1 |
| —CH$_2$— | O | Z19-1 |
| —CH$_2$— | O | Z19-2 |
| —CH$_2$— | O | Z19-3 |
| —CH$_2$— | O | Z19-4 |
| —CH$_2$— | O | Z19-5 |
| —CH$_2$— | O | Z19-6 |
| —CH$_2$— | O | Z19-7 |
| —CH$_2$— | O | Z19-8 |
| —CH$_2$— | O | Z20-1 |
| —CH$_2$— | O | Z21-1 |
| —CH$_2$— | O | Z21-2 |
| —CH$_2$— | O | Z21-3 |
| —CH$_2$— | O | Z22-1 |
| —CH$_2$— | O | Z22-2 |
| —CH$_2$— | O | Z23-1 |
| —CH$_2$— | O | Z24-1 |
| —CH$_2$— | O | Z25-1 |
| —CH$_2$— | O | Z26-1 |
| —CH$_2$— | O | Z27-1 |
| —CH$_2$— | O | Z28-1 |
| —CH$_2$— | O | Z29-1 |
| —CH$_2$— | O | Z30-1 |
| —CH$_2$— | O | Z33-1 |
| —CH$_2$— | — | Z1-1 |

TABLE 2-2-continued

| B | Y | Z |
|---|---|---|
| —CH₂— | — | Z2-1 |
| —CH₂— | — | Z2-2 |
| —CH₂— | — | Z2-3 |
| —CH₂— | — | Z2-4 |
| —CH₂— | — | Z2-5 |
| —CH₂— | — | Z2-6 |
| —CH₂— | — | Z2-7 |
| —CH₂— | — | Z2-8 |
| —CH₂— | — | Z2-9 |
| —CH₂— | — | Z2-10 |
| —CH₂— | — | Z2-11 |
| —CH₂— | — | Z2-12 |
| —CH₂— | — | Z2-13 |
| —CH₂— | — | Z2-14 |
| —CH₂— | — | Z2-15 |
| —CH₂— | — | Z2-16 |
| —CH₂— | — | Z2-17 |
| —CH₂— | — | Z2-18 |
| —CH₂— | — | Z2-19 |
| —CH₂— | — | Z2-20 |
| —CH₂— | — | Z2-21 |
| —CH₂— | — | Z2-22 |
| —CH₂— | — | Z2-39 |
| —CH₂— | — | Z2-40 |
| —CH₂— | — | Z2-41 |
| —CH₂— | — | Z3-1 |
| —CH₂— | — | Z3-2 |
| —CH₂— | — | Z3-3 |
| —CH₂— | — | Z3-4 |
| —CH₂— | — | Z3-6 |
| —CH₂— | — | Z3-7 |
| —CH₂— | — | Z3-8 |
| —CH₂— | — | Z3-9 |
| —CH₂— | — | Z4-1 |
| —CH₂— | — | Z4-2 |
| —CH₂— | — | Z4-3 |
| —CH₂— | — | Z4-4 |
| —CH₂— | — | Z4-5 |
| —CH₂— | — | Z8-1 |
| —CH₂— | — | Z8-2 |
| —CH₂— | — | Z8-3 |
| —CH₂— | — | Z8-4 |
| —CH₂— | — | Z8-5 |
| —CH₂— | — | Z8-6 |
| —CH₂— | — | Z8-7 |
| —CH₂— | — | Z8-8 |
| —CH₂— | — | Z8-9 |
| —CH₂— | — | Z8-10 |
| —CH₂— | — | Z8-11 |
| —CH₂— | — | Z22-1 |
| —CH₂— | — | Z22-2 |
| —CH₂— | — | Z23-1 |
| —CH₂— | — | Z24-1 |
| —CH₂— | — | Z25-1 |
| —CH₂— | — | Z26-1 |
| —CH₂— | — | Z27-1 |
| —CH₂— | — | Z28-1 |
| —CH₂— | — | Z29-1 |
| —CH₂— | — | Z30-1 |
| —CH₂— | — | Z33-1 |
| —CH₂— | — | Z35-1 |
| —CH₂CH₂— | O | Z2-1 |
| —CH₂CH₂— | O | Z2-2 |
| —CH₂CH₂— | O | Z2-3 |
| —CH₂CH₂— | O | Z2-4 |
| —CH₂CH₂— | O | Z2-5 |
| —CH₂CH₂— | O | Z2-6 |
| —CH₂CH₂— | O | Z2-7 |
| —CH₂CH₂— | O | Z2-8 |
| —CH₂CH₂— | O | Z2-9 |
| —CH₂CH₂— | O | Z2-10 |
| —CH₂CH₂— | O | Z2-11 |
| —CH₂CH₂— | O | Z2-12 |
| —CH₂CH₂— | O | Z2-13 |
| —CH₂CH₂— | O | Z2-14 |
| —CH₂CH₂— | O | Z2-15 |
| —CH₂CH₂— | O | Z2-16 |
| —CH₂CH₂— | O | Z2-17 |
| —CH₂CH₂— | O | Z2-18 |
| —CH₂CH₂— | O | Z2-19 |
| —CH₂CH₂— | O | Z2-20 |
| —CH₂CH₂— | O | Z2-21 |
| —CH₂CH₂— | O | Z2-22 |
| —CH₂CH₂— | O | Z2-39 |
| —CH₂CH₂— | O | Z2-40 |
| —CH₂CH₂— | O | Z2-41 |
| —CH₂CH₂— | O | Z3-1 |
| —CH₂CH₂— | O | Z3-2 |
| —CH₂CH₂— | O | Z3-3 |
| —CH₂CH₂— | O | Z3-4 |
| —CH₂CH₂— | O | Z3-6 |
| —CH₂CH₂— | O | Z3-7 |
| —CH₂CH₂— | O | Z3-8 |
| —CH₂CH₂— | O | Z3-9 |
| —CH₂CH₂— | O | Z4-1 |
| —CH₂CH₂— | O | Z4-2 |
| —CH₂CH₂— | O | Z4-3 |
| —CH₂CH₂— | O | Z4-4 |
| —CH₂CH₂— | O | Z4-5 |
| —CH₂CH₂— | O | Z8-1 |
| —CH₂CH₂— | O | Z8-2 |
| —CH₂CH₂— | O | Z8-3 |
| —CH₂CH₂— | O | Z8-4 |
| —CH₂CH₂— | O | Z8-5 |
| —CH₂CH₂— | O | Z8-6 |
| —CH₂CH₂— | O | Z8-7 |
| —CH₂CH₂— | O | Z8-8 |
| —CH₂CH₂— | O | Z8-9 |
| —CH₂CH₂— | O | Z8-10 |
| —CH₂CH₂— | O | Z8-11 |
| —CH₂CH₂— | O | Z11-1 |
| —CH₂CH₂— | O | Z11-3 |
| —CH₂CH₂— | — | Z2-1 |
| —CH₂CH₂— | — | Z2-2 |
| —CH₂CH₂— | — | Z2-3 |
| —CH₂CH₂— | — | Z2-4 |
| —CH₂CH₂— | — | Z2-5 |
| —CH₂CH₂— | — | Z2-6 |
| —CH₂CH₂— | — | Z2-7 |
| —CH₂CH₂— | — | Z2-8 |
| —CH₂CH₂— | — | Z2-9 |
| —CH₂CH₂— | — | Z2-10 |
| —CH₂CH₂— | — | Z2-11 |
| —CH₂CH₂— | — | Z2-12 |
| —CH₂CH₂— | — | Z2-13 |
| —CH₂CH₂— | — | Z2-14 |
| —CH₂CH₂— | — | Z2-14 |
| —CH₂CH₂— | — | Z2-15 |
| —CH₂CH₂— | — | Z2-16 |
| —CH₂CH₂— | — | Z2-17 |
| —CH₂CH₂— | — | Z2-18 |
| —CH₂CH₂— | — | Z2-19 |
| —CH₂CH₂— | — | Z2-20 |
| —CH₂CH₂— | — | Z2-21 |
| —CH₂CH₂— | — | Z2-22 |
| —CH₂CH₂— | — | Z2-39 |
| —CH₂CH₂— | — | Z2-40 |
| —CH₂CH₂— | — | Z2-41 |
| —CH₂CH₂— | — | Z3-1 |
| —CH₂CH₂— | — | Z3-2 |
| —CH₂CH₂— | — | Z3-3 |
| —CH₂CH₂— | — | Z3-4 |
| —CH₂CH₂— | — | Z3-6 |
| —CH₂CH₂— | — | Z3-7 |
| —CH₂CH₂— | — | Z3-8 |
| —CH₂CH₂— | — | Z3-9 |
| —CH₂CH₂— | — | Z4-1 |
| —CH₂CH₂— | — | Z4-2 |
| —CH₂CH₂— | — | Z4-3 |
| —CH₂CH₂— | — | Z4-4 |
| —CH₂CH₂— | — | Z4-5 |
| —CH₂CH₂— | — | Z8-1 |
| —CH₂CH₂— | — | Z8-2 |
| —CH₂CH₂— | — | Z8-3 |

TABLE 2-2-continued

| B | Y | Z |
|---|---|---|
| —CH₂CH₂— | — | Z8-4 |
| —CH₂CH₂— | — | Z8-5 |
| —CH₂CH₂— | — | Z8-6 |
| —CH₂CH₂— | — | Z8-7 |
| —CH₂CH₂— | — | Z8-8 |
| —CH₂CH₂— | — | Z8-9 |
| —CH₂CH₂— | — | Z8-10 |
| —CH₂CH₂— | — | Z8-11 |
| —CH₂CH₂— | — | Z22-1 |
| —CH₂CH₂— | — | Z22-2 |
| —CH₂CH₂— | — | Z23-1 |
| —CH₂CH₂— | O | Z22-1 |
| —CH₂CH₂— | O | Z22-2 |
| —CH₂CH₂— | O | Z23-1 |
| —(CH₂)₃— | — | Z2-1 |
| —(CH₂)₃— | — | Z2-2 |
| —(CH₂)₃— | — | Z2-3 |
| —(CH₂)₃— | — | Z2-4 |
| —(CH₂)₃— | — | Z2-5 |
| —(CH₂)₃— | — | Z2-6 |
| —(CH₂)₃— | — | Z2-7 |
| —(CH₂)₃— | — | Z2-8 |
| —(CH₂)₃— | — | Z2-9 |
| —(CH₂)₃— | — | Z2-10 |
| —(CH₂)₃— | — | Z2-11 |
| —(CH₂)₃— | — | Z2-12 |
| —(CH₂)₃— | — | Z2-13 |
| —(CH₂)₃— | — | Z2-14 |
| —(CH₂)₃— | — | Z2-15 |
| —(CH₂)₃— | — | Z2-16 |
| —(CH₂)₃— | — | Z2-17 |
| —(CH₂)₃— | — | Z2-18 |
| —(CH₂)₃— | — | Z2-19 |
| —(CH₂)₃— | — | Z2-20 |
| —(CH₂)₃— | — | Z2-21 |
| —(CH₂)₃— | — | Z2-22 |
| —(CH₂)₃— | — | Z2-39 |
| —(CH₂)₃— | — | Z2-40 |
| —(CH₂)₃— | — | Z2-41 |
| —(CH₂)₃— | — | Z3-1 |
| —(CH₂)₃— | — | Z3-2 |
| —(CH₂)₃— | — | Z3-3 |
| —(CH₂)₃— | — | Z3-4 |
| —(CH₂)₃— | — | Z3-6 |
| —(CH₂)₃— | — | Z3-7 |
| —(CH₂)₃— | — | Z3-8 |
| —(CH₂)₃— | — | Z3-9 |
| —(CH₂)₃— | — | Z4-1 |
| —(CH₂)₃— | — | Z4-2 |
| —(CH₂)₃— | — | Z4-3 |
| —(CH₂)₃— | — | Z4-4 |
| —(CH₂)₃— | — | Z4-5 |
| —(CH₂)₃— | — | Z8-1 |
| —(CH₂)₃— | — | Z8-2 |
| —(CH₂)₃— | — | Z8-3 |
| —(CH₂)₃— | — | Z8-4 |
| —(CH₂)₃— | — | Z8-5 |
| —(CH₂)₃— | — | Z8-6 |
| —(CH₂)₃— | — | Z8-7 |
| —(CH₂)₃— | — | Z8-8 |
| —(CH₂)₃— | — | Z8-9 |
| —(CH₂)₃— | — | Z8-10 |
| —(CH₂)₃— | — | Z8-11 |
| —(CH₂)₃— | — | Z22-1 |
| —(CH₂)₃— | — | Z22-2 |
| —(CH₂)₃— | — | Z23-1 |
| —(CH₂)₃— | — | Z33-1 |
| —(CH₂)₄— | — | Z2-1 |
| —(CH₂)₄— | — | Z2-2 |
| —(CH₂)₄— | — | Z2-3 |
| —(CH₂)₄— | — | Z2-4 |
| —(CH₂)₄— | — | Z2-5 |
| —(CH₂)₄— | — | Z2-6 |
| —(CH₂)₄— | — | Z2-7 |
| —(CH₂)₄— | — | Z2-8 |
| —(CH₂)₄— | — | Z2-9 |
| —(CH₂)₄— | — | Z2-10 |
| —(CH₂)₄— | — | Z2-11 |
| —(CH₂)₄— | — | Z2-12 |
| —(CH₂)₄— | — | Z2-13 |
| —(CH₂)₄— | — | Z2-14 |
| —(CH₂)₄— | — | Z2-15 |
| —(CH₂)₄— | — | Z2-16 |
| —(CH₂)₄— | — | Z2-17 |
| —(CH₂)₄— | — | Z2-18 |
| —(CH₂)₄— | — | Z2-19 |
| —(CH₂)₄— | — | Z2-20 |
| —(CH₂)₄— | — | Z2-21 |
| —(CH₂)₄— | — | Z2-22 |
| —(CH₂)₄— | — | Z2-39 |
| —(CH₂)₄— | — | Z2-40 |
| —(CH₂)₄— | — | Z2-41 |
| —(CH₂)₄— | — | Z3-1 |
| —(CH₂)₄— | — | Z3-2 |
| —(CH₂)₄— | — | Z3-3 |
| —(CH₂)₄— | — | Z3-4 |
| —(CH₂)₄— | — | Z3-6 |
| —(CH₂)₄— | — | Z3-7 |
| —(CH₂)₄— | — | Z3-8 |
| —(CH₂)₄— | — | Z3-9 |
| —(CH₂)₄— | — | Z4-1 |
| —(CH₂)₄— | — | Z4-2 |
| —(CH₂)₄— | — | Z4-3 |
| —(CH₂)₄— | — | Z4-4 |
| —(CH₂)₄— | — | Z4-5 |
| —(CH₂)₄— | — | Z8-1 |
| —(CH₂)₄— | — | Z8-2 |
| —(CH₂)₄— | — | Z8-3 |
| —(CH₂)₄— | — | Z8-4 |
| —(CH₂)₄— | — | Z8-5 |
| —(CH₂)₄— | — | Z8-6 |
| —(CH₂)₄— | — | Z8-7 |
| —(CH₂)₄— | — | Z8-8 |
| —(CH₂)₄— | — | Z8-9 |
| —(CH₂)₄— | — | Z8-10 |
| —(CH₂)₄— | — | Z8-11 |
| —(CH₂)₄— | — | Z22-1 |
| —(CH₂)₄— | — | Z22-2 |
| —(CH₂)₄— | — | Z23-1 |
| —(CH₂)₄— | — | Z33-1 |
| —(CH₂)₄— | — | Z35-1 |
| —CH₂— | S | Z2-1 |
| —CH₂— | S | Z2-2 |
| —CH₂— | S | Z2-3 |
| —CH₂— | S | Z2-4 |
| —CH₂— | S | Z22-1 |
| —CH₂— | S | Z22-2 |
| —CH₂— | S | Z23-1 |
| —CH₂— | S | Z2-5 |
| —CH₂— | S | Z2-6 |
| —CH₂— | S | Z2-7 |
| —CH₂— | S | Z2-8 |
| —CH₂— | S | Z2-9 |
| —CH₂— | S | Z2-10 |
| —CH₂— | S | Z2-11 |
| —CH₂— | S | Z2-12 |
| —CH₂— | S | Z2-13 |
| —CH₂— | S | Z2-14 |
| —CH₂— | S | Z2-15 |
| —CH₂— | S | Z2-16 |
| —CH₂— | S | Z2-17 |
| —CH₂— | S | Z2-18 |
| —CH₂— | S | Z2-19 |
| —CH₂— | S | Z2-20 |
| —CH₂— | S | Z2-21 |
| —CH₂— | S | Z2-22 |
| —CH₂— | S | Z2-39 |
| —CH₂— | S | Z2-40 |
| —CH₂— | S | Z2-41 |
| —CH₂— | S | Z3-1 |
| —CH₂— | S | Z3-2 |
| —CH₂— | S | Z3-3 |
| —CH₂— | S | Z3-4 |
| —CH₂— | S | Z3-6 |

TABLE 2-2-continued

| B | Y | Z |
|---|---|---|
| —CH₂— | S | Z3-7 |
| —CH₂— | S | Z3-8 |
| —CH₂— | S | Z3-9 |
| —CH₂— | S | Z4-1 |
| —CH₂— | S | Z4-2 |
| —CH₂— | S | Z4-3 |
| —CH₂— | S | Z4-4 |
| —CH₂— | S | Z4-5 |
| —CH₂— | S | Z6-1 |
| —CH₂— | S | Z8-1 |
| —CH₂— | S | Z8-2 |
| —CH₂— | S | Z8-3 |
| —CH₂— | S | Z8-4 |
| —CH₂— | S | Z8-5 |
| —CH₂— | S | Z8-6 |
| —CH₂— | S | Z8-7 |
| —CH₂— | S | Z8-8 |
| —CH₂— | S | Z8-9 |
| —CH₂— | S | Z8-10 |
| —CH₂— | S | Z8-11 |
| —CH₂CH₂— | C=O | Z2-1 |
| —CH₂CH₂— | C=O | Z2-2 |
| —CH₂CH₂— | C=O | Z2-3 |
| —CH₂CH₂— | C=O | Z2-4 |
| —CH₂CH₂— | C=O | Z2-5 |
| —CH₂CH₂— | C=O | Z2-6 |
| —CH₂CH₂— | C=O | Z2-7 |
| —CH₂CH₂— | C=O | Z2-8 |
| —CH₂CH₂— | C=O | Z2-9 |
| —CH₂CH₂— | C=O | Z2-10 |
| —CH₂CH₂— | C=O | Z2-11 |
| —CH₂CH₂— | C=O | Z2-12 |
| —CH₂CH₂— | C=O | Z2-13 |
| —CH₂CH₂— | C=O | Z2-14 |
| —CH₂CH₂— | C=O | Z2-15 |
| —CH₂CH₂— | C=O | Z2-16 |
| —CH₂CH₂— | C=O | Z2-17 |
| —CH₂CH₂— | C=O | Z2-18 |
| —CH₂CH₂— | C=O | Z2-19 |
| —CH₂CH₂— | C=O | Z2-20 |
| —CH₂CH₂— | C=O | Z2-21 |
| —CH₂CH₂— | C=O | Z2-22 |
| —CH₂CH₂— | C=O | Z2-39 |
| —CH₂CH₂— | C=O | Z2-40 |
| —CH₂CH₂— | C=O | Z2-41 |
| —CH₂CH₂— | C=O | Z3-1 |
| —CH₂CH₂— | C=O | Z3-2 |
| —CH₂CH₂— | C=O | Z3-3 |
| —CH₂CH₂— | C=O | Z3-4 |
| —CH₂CH₂— | C=O | Z3-6 |
| —CH₂CH₂— | C=O | Z3-7 |
| —CH₂CH₂— | C=O | Z3-8 |
| —CH₂CH₂— | C=O | Z3-9 |
| —CH₂CH₂— | C=O | Z4-1 |
| —CH₂CH₂— | C=O | Z4-2 |
| —CH₂CH₂— | C=O | Z4-3 |
| —CH₂CH₂— | C=O | Z4-4 |
| —CH₂CH₂— | C=O | Z4-5 |
| —CH₂CH₂— | C=O | Z6-1 |
| —CH₂CH₂— | C=O | Z8-1 |
| —CH₂CH₂— | C=O | Z8-2 |
| —CH₂CH₂— | C=O | Z8-3 |
| —CH₂CH₂— | C=O | Z8-4 |
| —CH₂CH₂— | C=O | Z8-5 |
| —CH₂CH₂— | C=O | Z8-6 |
| —CH₂CH₂— | C=O | Z8-7 |
| —CH₂CH₂— | C=O | Z8-8 |
| —CH₂CH₂— | C=O | Z8-9 |
| —CH₂CH₂— | C=O | Z8-10 |
| —CH₂CH₂— | C=O | Z8-11 |
| —CH₂CH₂— | C=O | Z26-1 |
| —CH=CH— | — | Z2-1 |
| —CH=CH— | — | Z2-2 |
| —CH=CH— | — | Z2-3 |
| —CH=CH— | — | Z2-4 |
| —CH=CH— | — | Z2-5 |
| —CH=CH— | — | Z2-6 |
| —CH=CH— | — | Z2-7 |
| —CH=CH— | — | Z2-8 |
| —CH=CH— | — | Z2-9 |
| —CH=CH— | — | Z2-10 |
| —CH=CH— | — | Z2-11 |
| —CH=CH— | — | Z2-12 |
| —CH=CH— | — | Z2-13 |
| —CH=CH— | — | Z2-14 |
| —CH=CH— | — | Z2-15 |
| —CH=CH— | — | Z2-16 |
| —CH=CH— | — | Z2-17 |
| —CH=CH— | — | Z2-18 |
| —CH=CH— | — | Z2-19 |
| —CH=CH— | — | Z2-20 |
| —CH=CH— | — | Z2-21 |
| —CH=CH— | — | Z2-22 |
| —CH=CH— | — | Z2-39 |
| —CH=CH— | — | Z2-40 |
| —CH=CH— | — | Z2-41 |
| —CH=CH— | — | Z3-1 |
| —CH=CH— | — | Z3-2 |
| —CH=CH— | — | Z3-3 |
| —CH=CH— | — | Z3-4 |
| —CH=CH— | — | Z3-6 |
| —CH=CH— | — | Z3-7 |
| —CH=CH— | — | Z3-8 |
| —CH=CH— | — | Z3-9 |
| —CH=CH— | — | Z4-1 |
| —CH=CH— | — | Z4-2 |
| —CH=CH— | — | Z4-3 |
| —CH=CH— | — | Z4-4 |
| —CH=CH— | — | Z4-5 |
| —CH=CH— | — | Z6-1 |
| —CH=CH— | — | Z8-1 |
| —CH=CH— | — | Z8-2 |
| —CH=CH— | — | Z8-3 |
| —CH=CH— | — | Z8-4 |
| —CH=CH— | — | Z8-5 |
| —CH=CH— | — | Z8-6 |
| —CH=CH— | — | Z8-7 |
| —CH=CH— | — | Z8-8 |
| —CH=CH— | — | Z8-9 |
| —CH=CH— | — | Z8-10 |
| —CH=CH— | — | Z8-11 |
| —(CH₂)₅— | — | Z2-1 |
| —(CH₂)₅— | — | Z2-2 |
| —(CH₂)₅— | — | Z2-3 |
| —(CH₂)₅— | — | Z2-4 |
| —(CH₂)₅— | — | Z2-5 |
| —(CH₂)₅— | — | Z2-6 |
| —(CH₂)₅— | — | Z2-7 |
| —(CH₂)₅— | — | Z2-8 |
| —(CH₂)₅— | — | Z2-9 |
| —(CH₂)₅— | — | Z2-10 |
| —(CH₂)₅— | — | Z2-11 |
| —(CH₂)₅— | — | Z2-12 |
| —(CH₂)₅— | — | Z2-13 |
| —(CH₂)₅— | — | Z2-14 |
| —(CH₂)₅— | — | Z2-15 |
| —(CH₂)₅— | — | Z2-16 |
| —(CH₂)₅— | — | Z2-17 |
| —(CH₂)₅— | — | Z2-18 |
| —(CH₂)₅— | — | Z2-19 |
| —(CH₂)₅— | — | Z2-20 |
| —(CH₂)₅— | — | Z2-21 |
| —(CH₂)₅— | — | Z2-22 |
| —(CH₂)₅— | — | Z2-39 |
| —(CH₂)₅— | — | Z2-40 |
| —(CH₂)₅— | — | Z2-41 |
| —(CH₂)₅— | — | Z3-1 |
| —(CH₂)₅— | — | Z3-2 |
| —(CH₂)₅— | — | Z3-3 |
| —(CH₂)₅— | — | Z3-4 |
| —(CH₂)₅— | — | Z3-6 |
| —(CH₂)₅— | — | Z3-7 |
| —(CH₂)₅— | — | Z3-8 |
| —(CH₂)₅— | — | Z3-9 |

TABLE 2-2-continued

| B | Y | Z |
|---|---|---|
| —(CH$_2$)$_5$— | — | Z4-1 |
| —(CH$_2$)$_5$— | — | Z4-2 |
| —(CH$_2$)$_5$— | — | Z4-3 |
| —(CH$_2$)$_5$— | — | Z4-4 |
| —(CH$_2$)$_5$— | — | Z4-5 |
| —(CH$_2$)$_5$— | — | Z6-1 |
| —(CH$_2$)$_5$— | — | Z8-1 |
| —(CH$_2$)$_5$— | — | Z8-2 |
| —(CH$_2$)$_5$— | — | Z8-3 |
| —(CH$_2$)$_5$— | — | Z8-4 |
| —(CH$_2$)$_5$— | — | Z8-5 |
| —(CH$_2$)$_5$— | — | Z8-6 |
| —(CH$_2$)$_5$— | — | Z8-7 |
| —(CH$_2$)$_5$— | — | Z8-8 |
| —(CH$_2$)$_5$— | — | Z8-9 |
| —(CH$_2$)$_5$— | — | Z8-10 |
| —(CH$_2$)$_5$— | — | Z8-11 |
| —CH$_2$— | C=O | Z2-1 |
| —CH$_2$— | C=O | Z2-2 |
| —CH$_2$— | C=O | Z2-3 |
| —CH$_2$— | C=O | Z2-4 |
| —CH$_2$— | C=O | Z2-5 |
| —CH$_2$— | C=O | Z2-6 |
| —CH$_2$— | C=O | Z2-7 |
| —CH$_2$— | C=O | Z2-8 |
| —CH$_2$— | C=O | Z2-9 |
| —CH$_2$— | C=O | Z2-10 |
| —CH$_2$— | C=O | Z2-11 |
| —CH$_2$— | C=O | Z2-12 |
| —CH$_2$— | C=O | Z2-13 |
| —CH$_2$— | C=O | Z2-14 |
| —CH$_2$— | C=O | Z2-15 |
| —CH$_2$— | C=O | Z2-16 |
| —CH$_2$— | C=O | Z2-17 |
| —CH$_2$— | C=O | Z2-18 |
| —CH$_2$— | C=O | Z2-19 |
| —CH$_2$— | C=O | Z2-20 |
| —CH$_2$— | C=O | Z2-21 |
| —CH$_2$— | C=O | Z2-22 |
| —CH$_2$— | C=O | Z2-39 |
| —CH$_2$— | C=O | Z2-40 |
| —CH$_2$— | C=O | Z2-41 |
| —CH$_2$— | C=O | Z3-1 |
| —CH$_2$— | C=O | Z3-2 |
| —CH$_2$— | C=O | Z3-3 |
| —CH$_2$— | C=O | Z3-4 |
| —CH$_2$— | C=O | Z3-6 |
| —CH$_2$— | C=O | Z3-7 |
| —CH$_2$— | C=O | Z3-8 |
| —CH$_2$— | C=O | Z3-9 |
| —CH$_2$— | C=O | Z4-1 |
| —CH$_2$— | C=O | Z4-2 |
| —CH$_2$— | C=O | Z4-3 |
| —CH$_2$— | C=O | Z4-4 |
| —CH$_2$— | C=O | Z4-5 |
| —CH$_2$— | C=O | Z6-1 |
| —CH$_2$— | C=O | Z8-1 |
| —CH$_2$— | C=O | Z8-2 |
| —CH$_2$— | C=O | Z8-3 |
| —CH$_2$— | C=O | Z8-4 |
| —CH$_2$— | C=O | Z8-5 |
| —CH$_2$— | C=O | Z8-6 |
| —CH$_2$— | C=O | Z8-7 |
| —CH$_2$— | C=O | Z8-8 |
| —CH$_2$— | C=O | Z8-9 |
| —CH$_2$— | C=O | Z8-10 |
| —CH$_2$— | C=O | Z8-11 |
| —CH$_2$— | SO$_2$ | Z2-1 |
| —CH$_2$— | SO$_2$ | Z2-2 |
| —CH$_2$— | SO$_2$ | Z2-3 |
| —CH$_2$— | SO$_2$ | Z2-4 |
| —CH$_2$— | SO$_2$ | Z2-5 |
| —CH$_2$— | SO$_2$ | Z2-6 |
| —CH$_2$— | SO$_2$ | Z2-7 |
| —CH$_2$— | SO$_2$ | Z2-8 |
| —CH$_2$— | SO$_2$ | Z2-9 |
| —CH$_2$— | SO$_2$ | Z2-10 |
| —CH$_2$— | SO$_2$ | Z2-11 |
| —CH$_2$— | SO$_2$ | Z2-12 |
| —CH$_2$— | SO$_2$ | Z2-13 |
| —CH$_2$— | SO$_2$ | Z2-14 |
| —CH$_2$— | SO$_2$ | Z2-15 |
| —CH$_2$— | SO$_2$ | Z2-16 |
| —CH$_2$— | SO$_2$ | Z2-17 |
| —CH$_2$— | SO$_2$ | Z2-18 |
| —CH$_2$— | SO$_2$ | Z2-19 |
| —CH$_2$— | SO$_2$ | Z2-20 |
| —CH$_2$— | SO$_2$ | Z2-21 |
| —CH$_2$— | SO$_2$ | Z2-22 |
| —CH$_2$— | SO$_2$ | Z2-39 |
| —CH$_2$— | SO$_2$ | Z2-40 |
| —CH$_2$— | SO$_2$ | Z2-41 |
| —CH$_2$— | SO$_2$ | Z3-1 |
| —CH$_2$— | SO$_2$ | Z3-2 |
| —CH$_2$— | SO$_2$ | Z3-3 |
| —CH$_2$— | SO$_2$ | Z3-4 |
| —CH$_2$— | SO$_2$ | Z3-6 |
| —CH$_2$— | SO$_2$ | Z3-7 |
| —CH$_2$— | SO$_2$ | Z3-8 |
| —CH$_2$— | SO$_2$ | Z3-9 |
| —CH$_2$— | SO$_2$ | Z4-1 |
| —CH$_2$— | SO$_2$ | Z4-2 |
| —CH$_2$— | SO$_2$ | Z4-3 |
| —CH$_2$— | SO$_2$ | Z4-4 |
| —CH$_2$— | SO$_2$ | Z4-5 |
| —CH$_2$— | SO$_2$ | Z6-1 |
| —CH$_2$— | SO$_2$ | Z8-1 |
| —CH$_2$— | SO$_2$ | Z8-2 |
| —CH$_2$— | SO$_2$ | Z8-3 |
| —CH$_2$— | SO$_2$ | Z8-4 |
| —CH$_2$— | SO$_2$ | Z8-5 |
| —CH$_2$— | SO$_2$ | Z8-6 |
| —CH$_2$— | SO$_2$ | Z8-7 |
| —CH$_2$— | SO$_2$ | Z8-8 |
| —CH$_2$— | SO$_2$ | Z8-9 |
| —CH$_2$— | SO$_2$ | Z8-10 |
| —CH$_2$— | SO$_2$ | Z8-11 |
| —CH$_2$— | NH | Z2-1 |
| —CH$_2$— | NH | Z2-2 |
| —CH$_2$— | NH | Z2-3 |
| —CH$_2$— | NH | Z2-4 |
| —CH$_2$— | NH | Z2-5 |
| —CH$_2$— | NH | Z2-6 |
| —CH$_2$— | NH | Z2-7 |
| —CH$_2$— | NH | Z2-8 |
| —CH$_2$— | NH | Z2-9 |
| —CH$_2$— | NH | Z2-10 |
| —CH$_2$— | NH | Z2-11 |
| —CH$_2$— | NH | Z2-12 |
| —CH$_2$— | NH | Z2-13 |
| —CH$_2$— | NH | Z2-14 |
| —CH$_2$— | NH | Z2-15 |
| —CH$_2$— | NH | Z2-16 |
| —CH$_2$— | NH | Z2-17 |
| —CH$_2$— | NH | Z2-18 |
| —CH$_2$— | NH | Z2-19 |
| —CH$_2$— | NH | Z2-20 |
| —CH$_2$— | NH | Z2-21 |
| —CH$_2$— | NH | Z2-22 |
| —CH$_2$— | NH | Z2-39 |
| —CH$_2$— | NH | Z2-40 |
| —CH$_2$— | NH | Z2-41 |
| —CH$_2$— | NH | Z3-1 |
| —CH$_2$— | NH | Z3-2 |
| —CH$_2$— | NH | Z3-3 |
| —CH$_2$— | NH | Z3-4 |
| —CH$_2$— | NH | Z3-6 |
| —CH$_2$— | NH | Z3-7 |
| —CH$_2$— | NH | Z3-8 |
| —CH$_2$— | NH | Z3-9 |
| —CH$_2$— | NH | Z4-1 |
| —CH$_2$— | NH | Z4-2 |
| —CH$_2$— | NH | Z4-3 |
| —CH$_2$— | NH | Z4-4 |

TABLE 2-2-continued

| B | Y | Z |
|---|---|---|
| —CH₂— | NH | Z4-5 |
| —CH₂— | NH | Z6-1 |
| —CH₂— | NH | Z8-1 |
| —CH₂— | NH | Z8-2 |
| —CH₂— | NH | Z8-3 |
| —CH₂— | NH | Z8-4 |
| —CH₂— | NH | Z8-5 |
| —CH₂— | NH | Z8-6 |
| —CH₂— | NH | Z8-7 |
| —CH₂— | NH | Z8-8 |
| —CH₂— | NH | Z8-9 |
| —CH₂— | NH | Z8-10 |
| —CH₂— | NH | Z8-11 |
| —CH₂— | NMe | Z2-1 |
| —CH₂— | NMe | Z2-2 |
| —CH₂— | NMe | Z2-3 |
| —CH₂— | NMe | Z2-4 |
| —CH₂— | NMe | Z2-5 |
| —CH₂— | NMe | Z2-6 |
| —CH₂— | NMe | Z2-7 |
| —CH₂— | NMe | Z2-8 |
| —CH₂— | NMe | Z2-9 |
| —CH₂— | NMe | Z2-10 |
| —CH₂— | NMe | Z2-11 |
| —CH₂— | NMe | Z2-12 |
| —CH₂— | NMe | Z2-13 |
| —CH₂— | NMe | Z2-14 |
| —CH₂— | NMe | Z2-15 |
| —CH₂— | NMe | Z2-16 |
| —CH₂— | NMe | Z2-17 |
| —CH₂— | NMe | Z2-18 |
| —CH₂— | NMe | Z2-19 |
| —CH₂— | NMe | Z2-20 |
| —CH₂— | NMe | Z2-21 |
| —CH₂— | NMe | Z2-22 |
| —CH₂— | NMe | Z2-39 |
| —CH₂— | NMe | Z2-40 |
| —CH₂— | NMe | Z2-41 |
| —CH₂— | NMe | Z3-1 |
| —CH₂— | NMe | Z3-2 |
| —CH₂— | NMe | Z3-3 |
| —CH₂— | NMe | Z3-4 |
| —CH₂— | NMe | Z3-6 |
| —CH₂— | NMe | Z3-7 |
| —CH₂— | NMe | Z3-8 |
| —CH₂— | NMe | Z3-9 |
| —CH₂— | NMe | Z4-1 |
| —CH₂— | NMe | Z4-2 |
| —CH₂— | NMe | Z4-3 |
| —CH₂— | NMe | Z4-4 |
| —CH₂— | NMe | Z4-5 |
| —CH₂— | NMe | Z6-1 |
| —CH₂— | NMe | Z8-1 |
| —CH₂— | NMe | Z8-2 |
| —CH₂— | NMe | Z8-3 |
| —CH₂— | NMe | Z8-4 |
| —CH₂— | NMe | Z8-5 |
| —CH₂— | NMe | Z8-6 |
| —CH₂— | NMe | Z8-7 |
| —CH₂— | NMe | Z8-8 |
| —CH₂— | NMe | Z8-9 |
| —CH₂— | NMe | Z8-10 |
| —CH₂— | NMe | Z8-11 |
| CH=CH—CH=CH | — | Z2-1 |
| CH=CH—CH=CH | — | Z2-2 |
| CH=CH—CH=CH | — | Z2-3 |
| CH=CH—CH=CH | — | Z2-4 |
| CH=CH—CH=CH | — | Z2-5 |
| CH=CH—CH=CH | — | Z2-6 |
| CH=CH—CH=CH | — | Z2-7 |
| CH=CH—CH=CH | — | Z2-8 |
| CH=CH—CH=CH | — | Z2-9 |
| CH=CH—CH=CH | — | Z2-10 |
| CH=CH—CH=CH | — | Z2-11 |
| CH=CH—CH=CH | — | Z2-12 |
| CH=CH—CH=CH | — | Z2-13 |
| CH=CH—CH=CH | — | Z2-14 |
| CH=CH—CH=CH | — | Z2-15 |
| CH=CH—CH=CH | — | Z2-16 |
| CH=CH—CH=CH | — | Z2-17 |
| CH=CH—CH=CH | — | Z2-18 |
| CH=CH—CH=CH | — | Z2-19 |
| CH=CH—CH=CH | — | Z2-20 |
| CH=CH—CR=CH | — | Z2-21 |
| CH=CH—CH=CH | — | Z2-22 |
| CH=CH—CH=CH | — | Z2-39 |
| CH=CH—CH=CH | — | Z2-40 |
| CH=CH—CH=CH | — | Z2-41 |
| CH=CH—CH=CH | — | Z3-1 |
| CH=CH—CH=CH | — | Z3-2 |
| CH=CH—CH=CH | — | Z3-3 |
| CH=CH—CH=CH | — | Z3-4 |
| CH=CH—CH=CH | — | Z3-6 |
| CH=CH—CH=CH | — | Z3-7 |
| CH=CH—CH=CH | — | Z3-8 |
| CH=CH—CH=CH | — | Z3-9 |
| CH=CH—CH=CH | — | Z3-10 |
| CH=CH—CH=CH | — | Z4-1 |
| CH=CH—CH=CH | — | Z4-2 |
| CH=CH—CH=CH | — | Z4-3 |
| CH=CH—CH=CH | — | Z4-4 |
| CH=CH—CH=CH | — | Z4-5 |
| CH=CH—CH=CH | — | Z8-1 |
| CH=CH—CH=CH | — | Z8-2 |
| CH=CH—CH=CH | — | Z8-3 |
| CH=CH—CH=CH | — | Z8-4 |
| CH=CH—CH=CH | — | Z8-5 |
| CH=CH—CH=CH | — | Z8-6 |
| CH=CH—CH=CH | — | Z8-7 |
| CH=CH—CH=CH | — | Z8-8 |
| CH=CH—CH=CH | — | Z8-9 |
| CH=CH—CH=CH | — | Z8-10 |
| CH=CH—CH=CH | — | Z8-11 |
| CH=CH—CH=CH | — | Z8-11 |
| CH=CH—CH=CH | — | Z8-11 |
| CH=CH—CH=CH | — | Z8-11 |
| CH=CH—CH=CH | — | Z8-11 |
| CH=CH—CH=CH | — | Z22-1 |
| CH=CH—CH=CH | — | Z22-2 |
| CH=CH—CH=CH | — | Z23-1 |

BEST MODE FOR CARRYING OUT THE INVENTION

Now, the present invention is further explained definitely with referring Examples and Reference Examples described below.

EXAMPLE 1

Preparation of (±)-(6-Hydroxy-2,5,7,8-tetramethylchroman-2-yl)-N-[4-(imidazol-1-yl)phenyl]carboxamide (Compound No. 3-1)

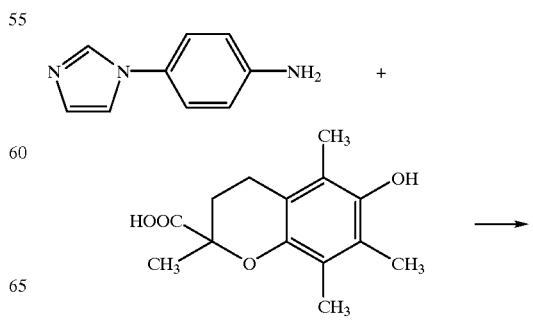

-continued

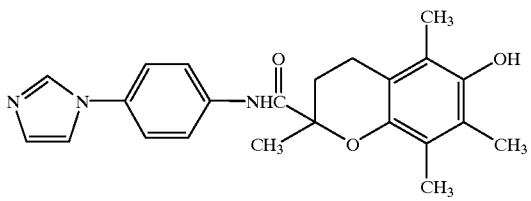

To a solution of (±)-6-hydroxy-2,5,7,,8-tetramethylchroman-2-carboxylic acid (4.0 g), 1-(4-aminophenyl)imidazole(2.82 g), 1-(3-dimethylaminopropyl)-3-ethylcarbodiimide hydrochloride (3.4 g) and 1-hydroxybenzotriazole (2.72 g) in DMF (30 ml) was added trimethylamine (2.5 ml) and the mixture was stirred at room temperature for 20 hours. The reaction mixture was poured into ice water and the precipitate was filtered and dissolved in chloroform. This solution was washed with brine, dried (MgSO$_4$) and evaporated to dryness. The residue was crystallized from chloroform-ether to obtain the title compound (3.85 g). m.p. 229–231° C.

EXAMPLE 2

Preparation of (±)-(6-hydroxy-2,5,7,8-tetramethylchroman-2-yl)-N-[4-(pyrrazol-5-yl)phenyl]carboxamide (Compound No. 3–25)

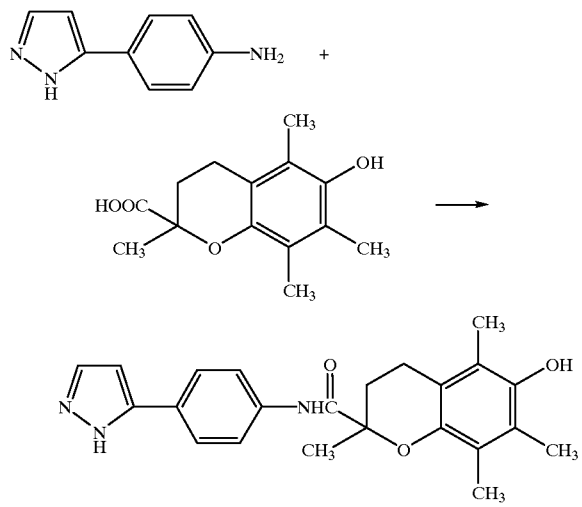

To a solution of (±)-6-hydroxy-2,5,7,,8-tetramethylchroman-2-carboxylic acid (1.0 g), 1-(4-aminophenyl)pyrazole(0.70 g),1-(3-dimethylaminopropyl)-3-ethylcarbodiimide hydrochloride (0.85 g) and 1-hydroxybenzotriazole(0.68 g) in DMF (8 ml) was added triethylamine (0.63 ml) and the mixture was stirred at room temperature for 20 hours and poured into ice water. The precipitate was filtered and dissolved in ethanol (10 ml) and 1N sodium hydroxide (10 ml) and heated under reflux for 1 hour. The reaction mixture was cooled, then neutralized with 1 N hydrochloric acid and extracted with chloroform. The extract was washed with brine, dried (MgSO$_4$) and evaporated to dryness. The residue was purified by column chromatography of silica gel (chloroform: methanol=100:3) to obtain the title compound 0.53 g). m.p. 215–218° C.

EXAMPLE 3

Preparation of (±)-2-[(6-hydroxy-2,5,7,8-tetramethylchroman-2-yl)-N-methylcarbonylamino]-N-[4-tetramethylchroman-2-yl)-N-methylcarbonylamino]-N-[4-(imadazol-1-yl)phenyl]acetamide (Compound No. 3–7)

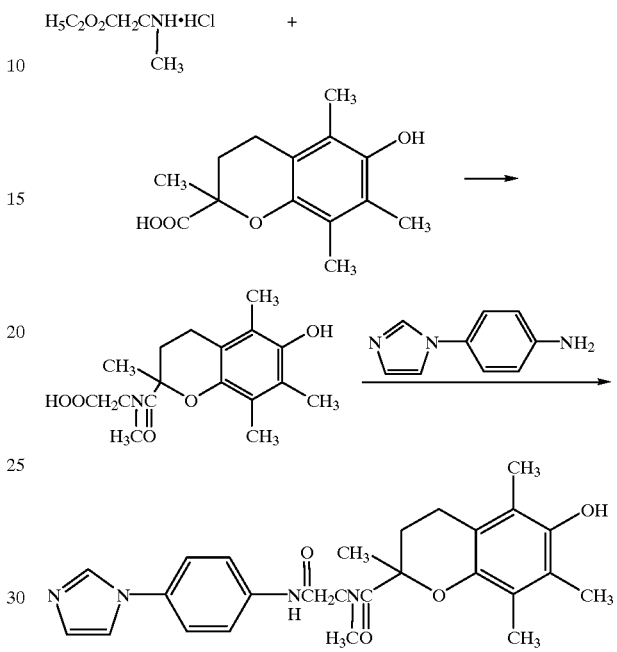

To a solution of (±)-6-hydroxy-2,5,7,8-tetramethylchroman-2-carboxylic acid (2.0 g), sarcosine ethyl ester hydrochloride (1.36 g), 1-(3-dimethylaminopropyl)-3-ethylcarbodiimide hydrochloride (1.70 g) and 1-hydroxybenzotriazole (1.36 g) in DMF (15 ml) was added triethylamine (2.5 ml) and the mixture was stirred at room temperature for 20 hours. The reaction mixture was poured into ice water and the precipitate was filtered and dissolved in chloroform-methanol. This solution was washed with brine, dried (MgSO$_4$) and evaporated to dryness. The residue was purified by column chromatography on silica gel (chloroform: methanol=100:3), and this intermediate was dissolved in ethanol (15 ml) and 1N sodium hydroxide (15 ml) and heated under reflux for 1 hour. The reaction mixture was cooled, then acidified with concentrated hydrochloric acid to pH 1, and extracted with chloroform. The extract was washed with brine, dried (magnesium sulfate) and evaporated to obtain a crude product (2.51 g). To this crude material (2.51 g), 1-(4-aminophenyl)imidazole(1.41 g), 1-(3-dimethylaminopropyl)-3-ethylcarbodiimide hydrochloride (1.71 g) and 1-hydroxybenzotriazole (1.36 g) in DMF (16 ml) was added triethylamine (1.26 ml) and the mixture was stirred at room temperature for 20 hours. The reaction mixture was poured into ice water and the precipitate was filtered and dissolved in chloroform-methanol. This solution was washed with brine, dried (MgSO$_4$) and evaporated to dryness. The residue was purified by column chromatography on silica gel (chloroform: methanol=100:3) to obtain the title compound (1.02 g, amorphous).

$^1$H NMR (CLCl$_3$, δppm): 1.7(s, 3H), 1.75(m, 1H), 2.05(s, 3H), 2.2 (s, 3H), 2.25(s, 3H), 2.5–2.9(m, 3H), 3.45(s, 3H), 3.75(d, 1H), 4.4(d, 1H), 7.1(s, 1H), 7.2–7.3(m, 3H), 7.7–7.8 (m, 3H)

EXAMPLE 4

Preparation of N-[4-(imidazol-1-yl)phenyl]-4-phenyl-4-(3,5,6-trimethyl-1,4-benzoquinon-2-yl)butanamide (Compound No. 3–27)

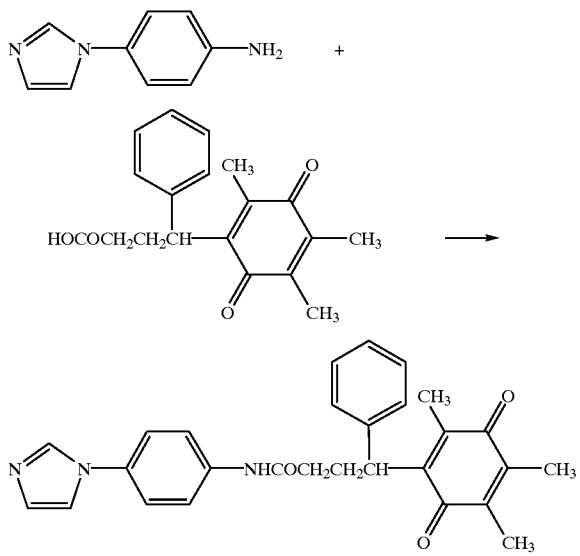

To a solution of 1-(4-aminophenyl)imidazole(0.71 g), 4-phenyl 4-(3,5,6-trimethyl-1,4-benzoquinon-2-yl)butanoic acid(1.25 g), ,1-(3-dimethylaminopropyl)-3-ethylcarbodiimide hydrochloride(0.85 g) and 1-hydroxybenzotriazole(0.85g) in DMF(8 ml) was added triethylamine(0.7 ml) and the mixture was stirred at room temperature for 20 hours. The reaction mixture was poured into ice water and the precipitate was filtered and dissolved in chloroform-methanol. This solution was washed with brine, dried (MgSO$_4$) and evaporated to dryness. The residue was purified by column chromatography on silica gel (chloroform: methanol=100:3) to obtain the title compound (0.82 g, amorphous).

$^1$H NMR (CDCl$_3$, δppm): 1.9(s, 6H), 2.05(s, 3H), 2.4–2.8 (m, 4H), 4.4(t, 1H), 7.1(s, 1H), 7.2–7.3(m, 9H), 7.65(d, 2H), 7.8(s, 1H), 8.25(s, 1H)

According to the same process as described in the Example 4, N-[4-(imidazol-1-yl)phenyl]-7-phenyl-4-(3,5,6-trimethyl-1,4-benzoquinon-2-yl)heptanamide (Compound No. 3–28).

1H-NMR (CLCl3, δppm): 1.2–1.8(m, 6H), 1.95(s, 3H), 2.0(s, 3H), 2.05(s, 3H), 2.1–2.4(m, 4H), 4.3 (t, 1H), 7.2–7.4 (m, 9H), 7.65(d, 2H), 7.75(s, 1H), 7.8(s, 1H)

EXAMPLE 5

Preparation of N-[4-(imidazol-1-yl)phenyl]-3-(3,5,6-trimethyl-1,4-benzoquinon-2-yl)propanamide (Compound No. 3–30)

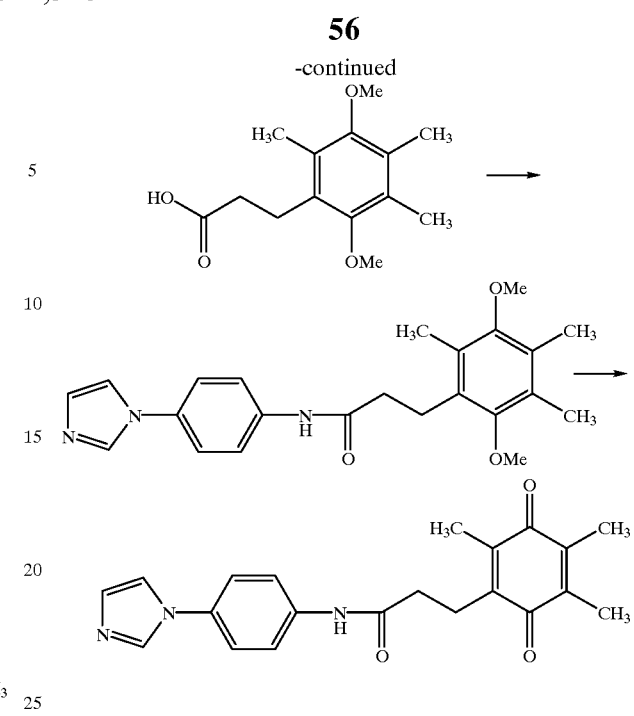

To a solution of 2,5-dimethoxy-3,4,6-trimethylphenylpropionic acid (1.91 g), 1-(4-aminophenyl)imidazole(1.35 g), 1-(3-dimethylaminopropyl)-3-ethylcarbodiimide hydrochloride(1.63 g) and 1-hydroxybenzotriazole(1.30 g) in DMF (30 ml) was added triethylamine(1.3 ml) and the mixture was stirred at room temperature for 20 hours. The reaction mixture was poured into ice water and the precipitate was filtered and dissolved in chloroform. This solution was washed with brine, dried (MgSO$_4$) and evaporated to dryness. The residue was crystallized from chloroform-ether to obtain N-[4-(imidazol-1-yl)phenyl]-3-(1,4-dimethoxy-3,5,6-trimethylphenyl)propanamide(2.89 g). To a suspension of this amide(1.01 g) and pyridine-2,6-dicarboxylic(1.30 g) in acetonitrile(18 ml) and water(4 ml) was added dropwise cerium ammonium nitrite(4.24 g) in water-acetonitrile(5 ml—5 ml) at 0? with stirring. After the addition was completed, the reaction mixture was stirred for 30 minutes at the same temperature and crystals precipitated were filtered. The crystals were dissolved in chloroform-methanol. This solution was washed with brine, dried(MgSO$_4$) and evaporated to dryness. The residue was purified by column chromatography on silica gel (chloroform: methanol=20:1) to obtain the title compound(0.89 g). m.p. 145–150° C.

EXAMPLE 6

Preparation of [4-(imidazol-1-yl)phenyl]-N-(3-pyridyloxy)acetamide (Compound No. 4–85)

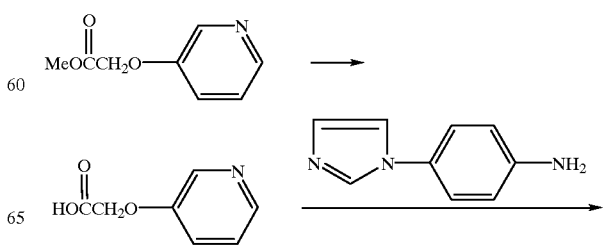

-continued

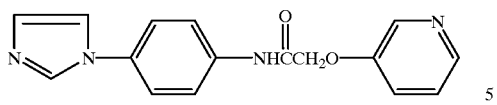

To a solution of 3-hydroxypyridine(5 g) in DMF(50 ml) was added slowly sodium hydride(2.1 g) under ice cooling. After the addition was completed, the reaction mixture was warmed up to room temperature and stirred at the same temperature for 30 minutes. The mixture was cooled with ice and methyl bromoacetate (8.1 g) was added slowly. After the addition was completed, the reaction mixture was stirred at room temperature for 15 hours and poured into ice water. The product was extracted with ethyl acetate, washed with brine, dried($MgSO_4$) and evaporated to dryness. The residue was purified by column chromatography on silica gel (chloroform: methanol=20:3) to obtain methyl 2-(3-pyridyloxy)acetate(1.7 g).

This acetate (1.7 g) was dissolved in methanol (10 ml) and 2.5N sodium hydroxide(10 ml) and heated at 60° C. for 2 hours and and evaporated, then it was acidified with 1N hydrochloric acid to pH 3, and crystals precipitate were filtered, washed with water and ethyl acetate and dried to obtain the title compound(0.14 g). m.p. 174° C.

EXAMPLE 7

Preparation of [4-(Imidazol-1-yl)phenyl]-N-(2-pyridyloxy)acetamide (Compound No. 4–83)

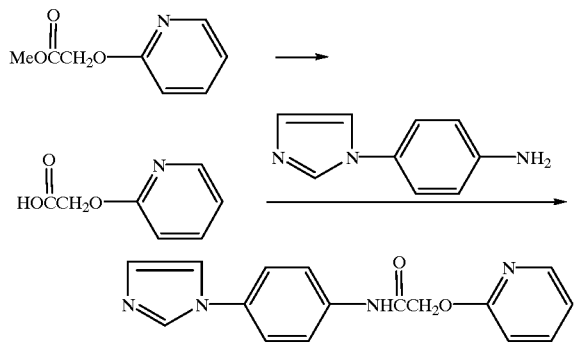

To a solution of 2-hydroxypyridine(5 g) in DMF(150 ml) was added silver oxide (I) (24 g) and methyl bromoacetate (20 g) and stirred at room temperature for 2 hours. After the catalyst was filtered off through celite, the filtrate was evaporated. The residue was dissolved in ethyl acetate and the solution was washed with brine, dried($MgSO_4$) and evaporated to dryness. The residue was purified by column chromatography on silica gel (chloroform: methanol=100:1) to obtain methyl 2-(2-pyridyloxy)acetate(1.0 g). According to the same manner as described above, the title compound was synthesized (0.1 g). m.p. 110° C.

REFERENCE EXAMPLE 1

Preparation of 5-(4-nitrophenyl)pyrazole

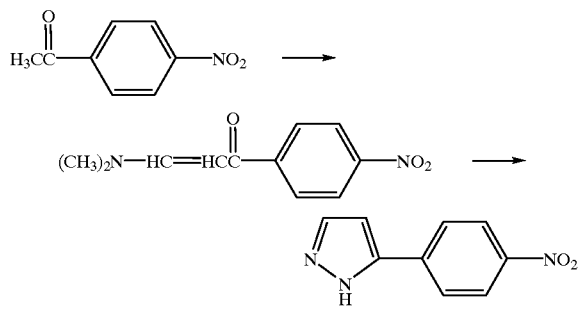

4-Nitroacetophenone(15 g) and N,N-dimethylformamide dimethylacetal(54 g) were refluxed for 1 hour. The reaction mixture was cooled, then crystals precipitate were filtered. To a solution of the crystals obtained (13.5 g) in ethanol (150 ml) was added hydrazine (4.52 g) and p-toluene sulfonic acid monohydrate (0.15 g) and the mixture was refluxed for 1 hours. The solvent was evaporated to dryness and the residue was crystallized from ether to obtain thr title compound (10.1 g).

REFERENCE EXAMPLE 2

Preparation of 5-(4-aminophenyl)pyrazole

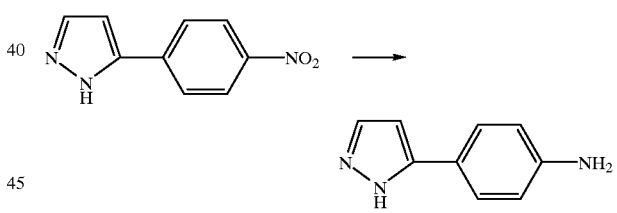

To a solution of 5-(4-nitrophenyl)pyrazole (10.1 g) in ethanol (100 ml) was added Tin(II) chloride dihydrate (35.7 g) and concentrated hydrochloric acid (25.5 ml). After the addition was completed, the reaction mixture was refluxed for 3 hours. After cooling, the solvent was evaporated and strongly basified (NaOH solution) and then extracted with chloroform. The extract was washed with brine, dried ($MgSO_4$) and evaporated to dryness to obtain the title compound (8.1 g).

The examples for the compounds according to the present invention including the compounds described in the examples described above are presented in Tables 3 and 4.

The marks and abbreviations in the tables represent as defined above.

TABLE 3

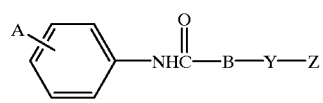

| Compound No. | A* | B | Y | Z | Physical Constant [ ] m.p. ° C. |
|---|---|---|---|---|---|
| 3-1 | 4-a1 | — | — | $h_1$ | [229–231] |
| 3-2 | 4-a1 | — | — | $h_2$ | [219–222] |
| 3-3 | 4-a1 | — | — | $h_3$ | [220–222] |
| 3-4 | 4-a1 | $CH_2$ | — | $h_1$ | [126–129] |
| 3-5 | 4-a1 | $CH_2CH_2$ | — | $h_1$ | [112–114] |
| 3-6 | 4-a1 | $CH(Me)CH_2$ | — | $h_1$ | [137–142] |
| 3-7 | 4-a1 | $CH_2$ | $N(Me)C(=O)$ | $h_1$ | amorphous&NMR1 |
| 3-8 | 4-a1 | $(CH_2)_5$ | $NHC(=O)$ | $h_1$ | [194–196] |
| 3-9 | 4-a1 | — | — | $h_4$ | [232–233] |
| 3-10 | 4-a1 | $CH_2CH_2$ | — | $h_4$ | [110–113] |
| 3-11 | 4-a1 | $CH_2CH_2$ | — | $h_6$ | [104–107] |
| 3-12 | 4-a1 | $(CH_2)_4$ | — | $h_4$ | [211–214] |
| 3-13 | 4-a1 | — | — | $h_9$ | [192–193] |
| 3-14 | 4-a1 | — | — | $h_8$ | [204–206] |
| 3-15 | 4-a1 | CH=CH | — | $h_4$ | [143–148] |
| 3-16 | 4-a1 | CH=CH—CH=CH | — | $h_4$ | [245–248] |
| 3-17 | 4-a1 | $(CH_2)_4$ | — | $h_1$ | [211–214] |
| 3-18 | 4-a1 | — | — | $h_{12}$ | [184–187] |
| 3-19 | 4-a2 | — | — | $h_9$ | [203–206] |
| 3-20 | 4-a1 | — | — | $h_7$ | amorphous&NMR2 |
| 3-21 | 3-a1 | — | — | $h_1$ | [207–210] |
| 3-22 | 2-a1 | — | — | $h_1$ | [191–196] |
| 3-23 | 4-a3 | — | — | $h_1$ | [203–206] |
| 3-24 | 4-a5 | — | — | $h_1$ | [166–167] |
| 3-25 | 4-a2 | — | — | $h_1$ | [215–218] |
| 3-26 | 4-a2 | $CH_2CH_2$ | — | $h_6$ | [195–196] |
| 3-27 | 4-a1 | $(CH_2)_2CH(Ph)$ | — | $h_{14}$ | amorphous&NMR3 |
| 3-28 | 4-a1 | $(CH_2)_5CH(Ph)$ | — | $h_{14}$ | amorphous&NMR4 |
| 3-29 | 4-a1 | $(CH_2)_4$ | — | $h_{14}$ | [140–143] |
| 3-30 | 4-a1 | $CH_2CH_2$ | — | $h_{14}$ | [145–150] |

Representing together the substitution site to the phenyl group.
& represents the NMR data are presented in Table 5.

TABLE 4

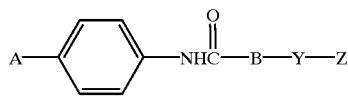

| Compound No. | A | B | Y | Z | Physical Constant [ ] m.p. ° C. |
|---|---|---|---|---|---|
| 4-1 | a1 | — | — | Z5-1 | [236–238] |
| 4-2 | a1 | — | — | Z2-1 | [260–261] |
| 4-3 | a1 | — | — | Z1-2 | [186] |
| 4-4 | a1 | — | — | Z2-2 | 230° C. dec. |
| 4-5 | a1 | — | — | Z2-3 | 260° C. dec. |
| 4-6 | a1 | — | — | Z2-4 | [240–242] |
| 4-7 | a1 | — | — | Z2-5 | [284] |
| 4-8 | a1 | — | — | Z2-7 | 280° C. dec. |
| 4-9 | a1 | — | — | Z2-9 | 270° C. dec. |
| 4-10 | a2 | — | — | Z2-1 | [285–287] |
| 4-11 | a1 | — | — | Z13-1 | [162–164] |
| 4-12 | a1 | — | — | Z13-4 | [197–198] |
| 4-13 | a1 | — | — | Z19-2 | 240° C. dec. |
| 4-14 | a1 | — | — | Z19-3 | [171] |
| 4-15 | a1 | — | — | Z19-5 | 240° C. dec. |
| 4-16 | a1 | — | — | Z19-6 | [225–227] |
| 4-17 | a1 | — | — | Z11-1 | [193–195] |
| 4-18 | a1 | — | — | Z11-2 | [156–158] |
| 4-19 | a1 | — | — | Z20-1 | [245–247] |
| 4-20 | a2 | — | — | Z11-1 | [158–160] |
| 4-21 | a1 | — | — | Z18-1 | [191] |
| 4-22 | a1 | — | — | Z9-1 | [164] |

TABLE 4-continued

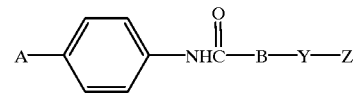

| Compound No. | A | B | Y | Z | Physical Constant [ ] m.p. ° C. |
|---|---|---|---|---|---|
| 4-23 | a1 | — | — | Z4-1 | 310° C. dec. |
| 4-24 | a1 | — | — | Z3-1 | [176–177] |
| 4-25 | a1 | — | — | Z3-2 | [255] |
| 4-26 | a1 | — | — | Z3-3 | [225–226] |
| 4-27 | a1 | — | — | Z3-4 | 250° C. dec. |
| 4-28 | a1 | — | — | Z3-5 | 280° C. dec. |
| 4-29 | a2 | — | — | Z3-3 | [229–231] |
| 4-30 | a1 | — | — | Z1-6 | 150° C. dec. |
| 4-31 | a1 | — | — | Z2-31 | [215–216] |
| 4-32 | a1 | — | — | Z12-1 | [231] |
| 4-33 | a1 | — | — | Z6-1 | [236] |
| 4-34 | a1 | — | — | Z21-1 | [265] |
| 4-35 | a1 | — | — | Z21-2 | [229] |
| 4-36 | a1 | — | — | Z14-1 | [269] |
| 4-37 | a1 | — | — | Z10-1 | [241] |
| 4-38 | a1 | — | — | Z1-3 | [210–212] |
| 4-39 | a1 | — | — | Z1-5 | [163] |
| 4-40 | a2 | — | — | Z2-31 | [163] |
| 4-41 | a1 | — | — | Z8-1 | [235] |
| 4-42 | a1 | — | — | Z8-2 | [218–220] |
| 4-43 | a1 | — | — | Z8-4 | [201–203] |
| 4-44 | a1 | — | — | Z8-6 | [300 up] |

TABLE 4-continued $$A-\text{C}_6\text{H}_4-\text{NHC}(=O)-B-Y-Z$$

| Compound No. | A | B | Y | Z | Physical Constant [ ] m.p. ° C. |
|---|---|---|---|---|---|
| 4-45 | a1 | — | — | Z8-1 | [242–244] |
| 4-46 | a1 | — | — | Z7-1 | 260° C. dec. |
| 4-47 | a1 | — | — | Z15-6 | [257–260] |
| 4-48 | a1 | — | — | Z1-8 | [178–179] |
| 4-59 | a1 | — | — | Z1-9 | [195] |
| 4-50 | a1 | — | — | Z1-11 | [153] |
| 4-51 | a2 | — | — | Z1-8 | [229] |
| 4-52 | a3 | — | — | Z1-8 | 250° C. dec. |
| 4-53 | a1 | — | — | Z1-10 | 260° C. dec. |
| 4-54 | a1 | — | — | Z3-10 | 194° C. dec. |
| 4-55 | a1 | — | — | Z8-7 | [218–219] |
| 4-56 | a1 | — | — | Z16-2 | [280] |
| 4-57 | a1 | — | — | Z11-3 | [218–219] |
| 4-58 | a1 | — | — | Z2-12 | amorphous&NMR5 |
| 4-59 | a1 | — | — | Z1-12 | 156° C. dec. |
| 4-60 | a1 | — | — | Z2-21 | 270° C. dec. |
| 4-61 | a1 | — | — | Z2-22 | [300 up] |
| 4-62 | a1 | — | — | Z2-37 | [192] |
| 4-63 | a1 | — | — | Z2-38 | [201] |
| 4-64 | a1 | — | — | Z2-39 | [208–210] |
| 4-65 | a1 | — | — | Z3-40 | [220] |
| 4-66 | a1 | — | — | Z8-9 | 296° C. dec. |
| 4-67 | a1 | — | — | Z8-10 | [189–190] |
| 4-68 | a1 | — | — | Z8-11 | [235–237] |
| 4-69 | a1 | — | — | Z9-2 | [249–250] |
| 4-70 | a1 | — | — | Z29-1 | [170–171] |
| 4-71 | a1 | — | — | Z30-1 | 220° C. dec. |
| 4-72 | a1 | CH$_2$ | — | Z25-1 | [182] |
| 4-73 | a1 | CH$_2$ | O | Z8-8 | [218–220] |
| 4-74 | a1 | CH$_2$ | — | Z2-11 | [222] |
| 4-75 | a1 | (CH$_2$)$_3$ | — | Z2-11 | [164] |
| 4-76 | a1 | CH$_2$ | O | Z14-1 | [240–242] |
| 4-77 | a1 | CH$_2$ | — | Z22-1 | [175–177] |
| 4-78 | a1 | CH$_2$ | — | Z22-2 | [190] |
| 4-79 | a1 | CH$_2$ | O | Z10-1 | 260° C. dec. |
| 4-80 | a1 | CH$_2$ | O | Z18-1 | [184–185] |
| 4-81 | a1 | CH$_2$ | O | Z5-2 | [198–200] |
| 4-82 | a1 | CH$_2$ | O | Z4-2 | [225] |
| 4-83 | a1 | CH$_2$ | O | Z3-1 | [110] |
| 4-84 | a1 | CH$_2$ | S | Z3-1 | [143] |
| 4-85 | a1 | CH$_2$ | O | Z3-3 | [174] |
| 4-86 | a1 | CH$_2$ | O | Z6-1 | [143] |
| 4-87 | a1 | CH$_2$ | S | Z6-1 | 210° C. dec. |
| 4-88 | a1 | CH$_2$ | O | Z16-1 | [258–260] |
| 4-89 | a1 | CH$_2$ | O | Z15-1 | [183–185] |
| 4-90 | a1 | (CH$_2$)$_2$ | — | Z3-3 | [178] |
| 4-91 | a2 | CH$_2$ | — | Z23-1 | [220–221] |
| 4-92 | a3 | CH$_2$ | — | Z24-1 | [192–194] |
| 4-93 | a1 | (CH$_2$)$_2$ | C=O | Z26-1 | [180] |
| 4-94 | a1 | CH$_2$ | — | Z28-1 | [100–105] |
| 4-95 | a1 | CH$_2$ | — | Z27-1 | [183] |
| 4-96 | a1 | CH$_2$ | O | Z8-1 | [175] |
| 4-97 | a1 | (CH$_2$)$_2$ | — | Z15-4 | [247–249] |
| 4-98 | a1 | —CH=CH— | — | Z1-82 | [190] |
| 4-99 | a1 | (CH$_2$)$_3$ | — | Z33-1 | 300° C. up |
| 4-100 | a1 | (CH$_2$)$_2$ | — | Z2-41 | [188–190] |
| 4-101 | a1 | CH$_2$ | O | Z4-3 | [134] |
| 4-102 | a1 | CH$_2$ | O | Z4-4 | [115] |
| 4-103 | a1 | CH$_2$ | O | Z4-5 | [215] |
| 4-104 | a1 | (CH$_2$)$_2$ | O | Z11-3 | [83–84] |
| 4-105 | a1 | (CH$_2$)$_4$ | — | Z35-1 | [83–85] |
| 4-106 | a1 | CH$_2$ | O | Z8-3 | [200–202] |

TABLE 5

| Compound No. | $^1$H-NMR (CDCl$_3$, δppm) |
|---|---|
| NMR1 3-7 | 1.7(s, 3H), 1.75(m, 1H), 2.05(s, 3H), 2.2(s, 3H), 2.25(s, 3H), 2.5–2.9(m, 3H), 3.45(s, 3H), 3.75(d, 1H), 4.4(d, 1H), 7.1(s, 1H), 7.2–7.3(m, 3H), 7.7–7.8(m, 3H) |
| NMR2 3-20 | 1.6(s, 3H), 2.0(m, 4H), 2.1(s, 3H), 2.3(s, 3H), 2.35(m, 4H), 2.7(m, 2H), 7.2(s, 1H), 7.25(S, 1H), 7.3(d, 2H), 7.6 (d, 2H), 7.8(s, 1H), 7.8(S, 1H), 8.4(br, 1H) |
| NMR3 3-27 | 1.9(s, 6H), 2.05(s, 3H), 2.4–2.8(m, 4H), 4.4(t, 1H), 7.1 (s, 1H) 7.2–7.3(m, 9H), 7.65(d, 2H), 7.8(s, 1H), 8.25(s, 1H) |
| NMR4 3-28 | 1.2–1.8(m, 6H), 1.95(s, 3H), 2.0(s, 3H), 2.05(s, 3H), 2.1–2.4(m, 4H), 4.3(t, 1H), 7.7.2–7.4(m, 9H), 7.65(d, 2H), 7.75(s, 1H), 7.8(s, 1H) |
| NMR5 4-5 | 3.85(s, 3H), 7.20(s, 1H), 7.25–7.40(m, 6H), 7.75–7.85 (m, 4H), 8.15(m, 1H), 8.45(br S, 1H) |

Now, examples for the pharmaceutical preparation comprising the compounds according to the present invention are given in the following.

EXAMPLE 4

Oral Preparation (Tablets Containing 10 mg Active Ingredient)

| | |
|---|---|
| Compound No. 1-1 | 10 mg |
| Lactose | 81.4 mg |
| Corn starch | 20 mg |
| Hydroxypropylcellulose | 4 mg |
| Potassium carboxymethylcellulose | 4 mg |
| Magnesium stearate | 0.6 mg |
| Total | 120 mg |

The Compound No. 1-1 (see Table 1) in an amount of 50 g, lactose in an amount of 407 g and corn starch in an amount of 100 g were homogeneously admixed by using fluid type granulator (manufactured by Ohgawara Seisakusho Co., Ltd.) so as to accord to the same composition ratio as shown above. The granulation was carried out after spraying aqueous solution of 10% hydroxypropylcellulose in an amount of 200 g to the mixture. After drying, the granules were passed through a sieve with 20 mesh and then added with potassium carboxymethylcellulose in an amount of 20 g and magnesium stearate in an amount of 3 g, and the mixture was then prepared into tablets each having 120 mg weight by using a rotary tablet preparator (manufactured by Hata Tekkosho Co., Ltd.) equipped with a mallet having a size of 7 mm×8.4R.

Industrial Use

Now, the excellent pharmacological effect of the compounds according to the present invention is explained with showing the test examples described below.

Pharmacological Test Example 1: Effect on serum lipids of cholesterol-fed hamsters Syrian hamsters (Std:Syrian, Male, 4 weeks old) were freely fed with chow containing 1% cholesterol and 10% coconut oil for 3 weeks ad libitum.

At the last week of feeding, each of the test compounds was dissolved or suspended in either 0.1% hydrochloric acid solution or 1% polyethylene-hydrogenated castor oil (NIKKOL HCO-60) solution and was orally administrated to hamsters once a day for 5 days. For the hamsters of the control group, only the solvent was orally administered.

Then, blood was collected from the abdominal vein under the condition of anesthesia with pentobarbital at 2–4 hours after the last administration, and the serum in the blood was separated. The serum total cholesterol value and the serum triglyceride value were determined by using autobiochemical analyzer with analizing kits, and reduction rate of the serum lipids was determined according to the equation indicated below based on the analyzed values for respective hamster groups.

Serum lipids reduction rate (%)=(Amount of serum lipids of the control group−Amount of serum lipids of the group administrated with the test compound)/Amount of serum lipids of the control group×100

The results are presented in Table 6.

TABLE 6

| Compound No. | Dose (mg/kg) | Serum lipids reduction rate comparing to Control group (%), Means of 3 animals | |
|---|---|---|---|
| | | Total cholesterol | Triglyceride |
| 3-1 | 25 | 40 | 62 |
| 3-4 | 25 | 37 | 80 |
| 3-9 | 25 | 38 | 49 |
| 3-10 | 25 | 35 | 51 |
| 3-11 | 25 | 42 | 55 |
| 3-14 | 25 | 22 | 31 |
| 3-15 | 25 | 26 | 30 |
| 3-20 | 25 | 31 | 41 |
| 3-28 | 25 | 29 | 23 |
| 4-2 | 12.5 | 32 | 45 |
| 4-3 | 25 | 75 | 91 |
| 4-4 | 12.5 | 23 | 32 |
| 4-6 | 12.5 | 41 | 71 |
| 4-7 | 25 | 27 | 31 |
| 4-8 | 25 | 37 | 73 |
| 4-9 | 25 | 44 | 61 |
| 4-11 | 25 | 43 | 47 |
| 4-12 | 25 | 27 | 41 |
| 4-14 | 25 | 66 | 42 |
| 4-15 | 12.5 | 37 | 73 |
| 4-16 | 25 | 34 | 34 |
| 4-17 | 12.5 | 35 | 53 |
| 4-19 | 25 | 19 | 50 |
| 4-21 | 25 | 51 | 57 |
| 4-22 | 25 | 48 | 61 |
| 4-24 | 12.5 | 30 | 25 |
| 4-25 | 12.5 | 25 | 52 |
| 4-26 | 6.25 | 22 | 48 |
| 4-27 | 25 | 40 | 46 |
| 4-28 | 12.5 | 24 | 34 |
| 4-31 | 25 | 46 | 59 |
| 4-32 | 25 | 58 | 68 |
| 4-33 | 12.5 | 35 | 44 |
| 4-34 | 25 | 37 | 39 |
| 4-37 | 12.5 | 26 | 25 |
| 4-38 | 12.5 | 32 | 31 |
| 4-39 | 25 | 25 | 45 |
| 4-41 | 25 | 50 | 67 |
| 4-44 | 25 | 21 | 31 |
| 4-46 | 25 | 52 | 45 |
| 4-48 | 25 | 76 | 85 |
| 4-62 | 25 | 42 | 59 |
| 4-63 | 25 | 26 | 29 |
| 4-66 | 25 | 55 | 66 |
| 4-70 | 25 | 34 | 48 |
| 4-71 | 25 | 45 | 62 |
| 4-72 | 25 | 37 | 53 |
| 4-73 | 25 | 34 | 50 |
| 4-79 | 12.5 | 29 | 45 |
| 4-80 | 25 | 40 | 52 |
| 4-81 | 12.5 | 22 | 43 |
| 4-85 | 25 | 39 | 44 |
| 4-87 | 25 | 34 | 37 |

TABLE 6-continued

| Compound No. | Dose (mg/kg) | Serum lipids reduction rate comparing to Control group (%), Means of 3 animals | |
|---|---|---|---|
| | | Total cholesterol | Triglyceride |
| 4-88 | 25 | 39 | 53 |
| 4-89 | 25 | 45 | 42 |
| 4-90 | 25 | 22 | 36 |
| 4-91 | 25 | 37 | 48 |
| 4-92 | 25 | 29 | 34 |
| 4-96 | 25 | 36 | 50 |
| 4-97 | 12.5 | 26 | 33 |
| 4-100 | 25 | 26 | 33 |
| 4-101 | 25 | 41 | 38 |
| 4-103 | 25 | 35 | 46 |
| 4-104 | 25 | 25 | 38 |
| reference* | 50 | 30 | 38 |

*For the reference, Fenofibrate was used for the positive control group.

Pharmacological Test Example 2: Effect on lipid peroxidation in vitro

Lipid peroxidation activity in rat liver microsome was determined according to the method of Malvy et al. (Malvy et al., Biochemical and Biophysical Research Communications, 95, 734–737 (1980)). More particularly, 500 $\mu$M cystein and 5 $\mu$M ferrous(II) sulfate were incubated with rat liver microsomes, and the amount of malonaldehyde produced due to the decomposition of lipid peroxide was determined according to thiobarbituric acid method. The concentration of the compounds required to inhibit the formation of lipid peroxide by 50% (IC50) was calculated. The results are presented in Table 7.

TABLE 7

| Compound No. | Lipid Antiperoxidation Activity 50% Inhibition Concentration (IC50, $\mu$M) |
|---|---|
| 3-1 | 2.7 |
| 3-4 | 2.3 |
| 3-5 | 1.3 |
| 3-8 | 3.8 |
| 3-9 | 1.9 |
| 3-10 | 2.1 |
| 3-11 | 2.3 |
| 3-12 | 2.5 |
| 3-13 | 2.8 |
| 3-14 | 2.6 |
| 3-15 | 0.92 |
| 3-16 | 2.1 |
| 3-19 | 0.42 |
| 3-20 | 2.7 |
| 3-25 | 0.49 |
| 3-26 | 0.25 |
| 3-28 | 3.3 |
| 3-29 | 2.7 |
| BHT* | 2.2 |

*BHT 2,6-t-Dibutyl-p-cresol

Pharmacological Test Example 3: Effect on lipid peroxidation in vitro

Effect of the compounds of the present invention on the produced lipid peroxide in liver was examined on carbon tetrachloride induced liver damage model in rats.

Briefly, providing 5 SD-strain male rats (6 weeks old) for each group, carbon tetrachloride at the rate of 1 ml/kg or 2 ml/kg (0.5 ml/kg or 1 ml/kg based on carbon tetrachloride) was orally administered to the rats together with the equivalent dose of olive oil. At 24 hours after the administration of carbon tetrachloride, their livers were excised, and the produced amount of lipid peroxide in liver was determined by thiobarbituric acid method according to Uchiyama's method (Uchiyama, M., et al., Analytical biochemistry, 86, 271–278 (1978)). In parallel, as the indicator for liver disorder due to carbon tetrachloride, serum enzyme activity (GOT, GPT) was measured.

Then each of the test compounds, which was either dissolved or suspended in either 0.1% hydrochloric acid solution or olive oil, was orally administered to the rats 3 times at 1 before and, 3 and 6 hours after the administration of carbon tetrachloride. For the rats of normal group and control groups, the solvent was orally administered. Based on the measured values for each groups, the inhibitory rate of producing peroxidized lipids and the inhibitory rate of causing liver disorder were calculated according to the following equation.

Inhibitory rate of producing lipid peroxide (%)=[1−(Produced amount of lipid peroxide in the test compound group−Produced amount of lipid peroxide in the normal rat group)/(Produced amount of lipid peroxide in the control group−Produced amount of lipid peroxide in the normal rat group)]×100

Liver disorder preventing rate (%)=[1−(GOT amount of GPT amount in the test compound group−GOT amount or GPT amount in the normal rat group)/(GOT amount or GPT amount in the control group−GOT amount or GPT amount in the normal rat group)]×100

The results are presented in Table 8.

against peroxidized lipid production, and therefore, they can be a remedy for arteriosclerosis.

In addition, the compounds of the present invention have excellent antioxidation activity and can prevent the causing of tissue disorder in ischemic lesions by removing various active oxygen and lipid peroxide, and therefore, they can be also a remedy for disorder of ischemic organs.

Further, according to the producing process specified in the present invention, the compounds represented by the general formula (1) can be produced advantageously in an industrial scale.

What is claimed is:

1. Phenylazole compounds and a pharmaceutically acceptable salt thereof represented by a

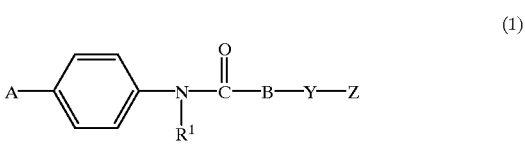

(1)

wherein $R^1$ represents hydrogen or optionally substituted $C_{1-6}$ alkyl,

A represents optionally substituted imidazolyl or optionally substituted pyrazolyl,

TABLE 8

| Compound No. | Dose (mg/kg) | Antioxidation Activity of Lipid | | Preventive Activity on Liver Disorder | | | |
|---|---|---|---|---|---|---|---|
| | | Mass of lipid peroxide ($A_{535nm}$/g lever) | Prevention Rate (%) | GOT | | GPT | |
| | | | | IU/L | Prevention Rate (%) | IU/L | Prevention Rate (%) |
| Normal rat | | 2.266 | | 138 | | 50 | |
| Control Rat | CCl$_4$: 0.5 ml/kg | 4.695 | | 428 | | 103 | |
| group 3-1 | 100 | 2.361 | 96 | 137 | 100 | 61 | 86 |
| Reference* | 100 | 2.116 | 100 | 351 | 27 | 117 | −26 |
| Control Rat | CCl$_4$: 1 ml/kg | 14.987 | | 1097 | | 443 | |
| group 3-28 | 10 | 5.781 | 61 | 269 | 76 | 82 | 82 |
| Control Rat | CCl$_4$: 1 ml/kg | 11.493 | | 1138 | | 280 | |
| group 3-29 | 10 | 2.440 | 79 | 273 | 76 | 85 | 70 |
| Control Rat | CCl$_4$: 1 ml/kg | 13.595 | | 701 | | 339 | |
| group Reference* | 100 | 2.382 | 82 | 871 | −24 | 373 | −10 |

*For the reference, Vitamine-E-acetate was used.

Pharmacological Test Example 4: Repeated Oral Administration Toxicity

The Compound with No. 3-1 was suspended in 1% polyethylene-hardened castor oil (NIKKOL HCO-60) solution, and the suspension was orally administered to rats (male SD-strain), 6 rats per group, at a rate of 100 mg/kg/day for 7 days. As the results, neither death nor any toxicological symptoms were observed.

As explained above, the compounds of the present invention are highly safe and capable of reducing the amounts of triglyceride in blood and cholesterol to an equivalent level, and are therefore noted as useful as a drug for hyperlipermia.

The compounds of the present invention can inhibit the causing and development of arteriosclerosis lesions since they have antioxidation activity and preventive activity

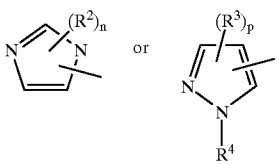

wherein $R^2$ and $R^3$ each independently represent optionally substituted $C_{1-6}$ alkyl, $R^4$ represents optionally substituted $C_{1-6}$ alkyl, $C_{1-6}$ alkylcarbonyl or benzoyl, n represents 0 or an integer of 1–3, p represents 0 or an integer of 1–2, and when both n and p are an integer of 2 or more, $R^2$ and $R^3$ may be the same of different, B represents a group represented by either one of the chemical structures given below:

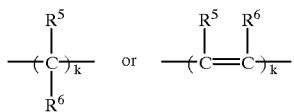

wherein $R^5$ and $R^6$ each independently represent hydrogen, cyano, hydroxy, halogeno, $C_{1-6}$ alkyl, $C_{1-6}$ alkoxy, $C_{2-6}$ alkenyl, $C_{2-6}$ alkynyl, $C_{2-6}$ alkenyloxy, $C_{2-6}$ alkynyloxy, $C_{1-6}$ acyloxy, $C_{3-6}$ cycloalkyl, or optionally substituted phenyl, k represents 0 or an integer of 1–15, provided $R^5$ and $R^6$ may be the same or different when k is an integer of 2 or more;

Y represents a bonding, or 0, S, $SO_2$, CO, $OCH_2$, $N(R^7)$ CO or $(NR^7)$, wherein $R^7$ represents hydrogen or optionally substituted $C_{1-6}$ alkyl;

Z represents optionally substituted chroman-2-yl, optionally substituted 2,3-dihydrobenzofuran-2-yl, optionally substituted thiochroman-2-yl, optionally substituted 2,3-dihydrobenzothiophen-2-yl, optionally substituted 1,3-benzoxathiol-2-yl, optionally substituted 1,4-benzoquinon-2-yl or optionally substituted 1,4-naphthoquinon-2-yl.

2. The compounds according to the claim 1, wherein Z is a group represented by any of chemical structures (A), (B) and (C) shown below;

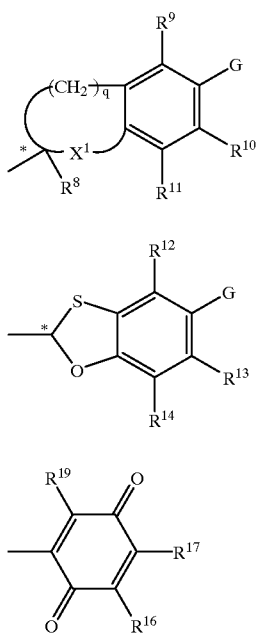

wherein * represents asymmetric carbon atom, X' represents oxygen or sulfur atom, and q represents 1 or 2, $R^8$, $R^9$, $R^{12}$, $R^{13}$ and $R^{14}$ each independently represent hydrogen or $C_{1-6}$ alkyl, and $R^{10}$ and $R^{11}$ each independently represent hydrogen, $C_{1-6}$ alkyl or $C_{1-6}$ alkoxy, G represents a group represented by either formula of $OR^{15}$ or $NHR^{16}$, wherein $R^{15}$ and $R^{16}$ each represent hydrogen, $C_{1-6}$ alkylcarbonyl or optionally substituted benzoyl, $R^{17}$ and $R^{18}$ each independently represent hydrogen, methyl or methoxy, or $R^{17}$ and $R^{18}$ may form a ring selected from a group consisting of

—$CH_2CH_2CH_2$—#, "—$CH_2CH$=$CH$—#, #—$CHCHCH_2$—#, #—$CH_2CH_2CH_2CH_2$—# or #—CH=CHCH=—CH—#, wherein # represents that these groups are bonding to a quinone ring at the site where $R^{17}$ and $R^{18}$ are bonding, and $R^{19}$ represents hydrogen or methyl.

3. The compounds represented by the general formula (1) as defined in claim 1, wherein A is 1-imidazolyl or 1H-pyrazol-5-yl.

4. A process for producing compounds represented by a general formula (1):

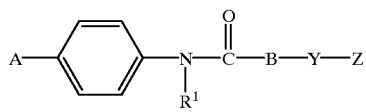

(1)

wherein the compounds are produced by dehydrating and condensing an amine compound represented by a general formula (2):

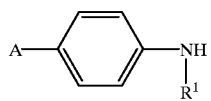

(2)

wherein A and $R^1$ are as defined in claim 1, and a carboxylic acid represented by a general formula (3);

HOOC—B—Y—Z wherein B, Y and Z are as defined i claim 1.

5. A process for producing compounds represented by a general formula (1');

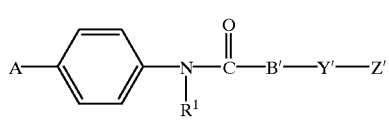

(1')

wherein A is as defined in claim 1, and B', Y' and Z' are respectively as defined for B, Y and Z in claim 1 except halogenated groups with a halogenating agent, such as hydroxy and amino, by halogenating a carboxylate compound represented by a general formula (3');

HOOC—B'—Y'—Z'          (3')

wherein R', Y' and Z' are as defined above, to prepare an acid chloride represented by a general formula (4);

ClOC—B'—Y'—Z'          (4)

wherein B', Y' and Z' are as defined above, and subjecting the obtained acid chloride to a reaction with an amine represented by the general formula (2) in claim 4.

6. A pharmaceutical composition comprising one or more compounds represented by the general formula (1) as defined in claim 1 and a pharmaceutically acceptable carrier as the active pharmaceutical ingredient.

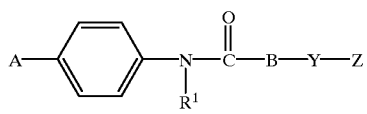

(1)

7. A pharmaceutical composition according to the claim 6, wherein the group represented by Z in the general formula (1) is optionally substituted chroman-2-yl, optionally substituted 2, 3-dihydrobenzofuran-2-yl, optionally substituted thiochroman-2-yl, optionally substituted 2, 3-dihydrobenzothiophen-2-yl, optionally substituted 1,3-benzoxathiol-2-yl, optionally substituted 1, 4-benzoquinon-2-yl or optionally substituted 1, 4-naphthoquinon-2-yl.

* * * * *

UNITED STATES PATENT AND TRADEMARK OFFICE
CERTIFICATE OF CORRECTION

PATENT NO.    : 6,342,516 B1  
DATED         : January 29, 2002  
INVENTOR(S)   : Nobuhiro Umeda et al.

It is certified that error appears in the above-identified patent and that said Letters Patent is hereby corrected as shown below:

Title page,  
Item [75], Inventors, delete inventors "Hirokazu Yamada and Kunihito Ito"  
Replace city of first four inventors with -- Kanagawa, Japan --.  
Replace city of fifth inventor with -- Hokkaido, Japan --.

Column 4,  
Line 5, replace "#—CH=CHCH$_{2-}$#" with -- #—CH=CHCH$_2$—# --  
Line 6, replace "#—CH$_2$CH$_2$CH$_2$CH$_2$—#" -- with #—CH$_2$CH$_2$CH$_2$CH$_2$—# --

Column 5,  
Line 48, replace "1–benzylpyrazol-4yl" with -- 1–benzylpyrazol-4-yl --.  
Line 58, replace "1methylallyl" with -- 1–methylallyl --.

Column 15,  
Line 13, replace "ranal" with -- renal --.

Column 24,  
Lines 40-45, replace "existing formula Z15-1" with -- 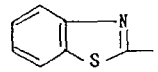 --

Column 52,  
Line 10, Table 2-2, under Column B, replace "CH=CH-CR=CH" with  
-- CH=CH-CH=CH --.

Column 54,  
Line 4, delete "N-[4-tetramethylchroman-2-yl)-N-"  
Line 5, delete "methylcarbonylamino]"  
Line 5, replace "-N-[4-(imadazol-1-yl)phenyl]" with -- -N-[4-(imidazol-1-yl)phenyl] --.  
Line 64, replace "$^1$H NMR (CLCl$_3$, δppm):" with -- $^1$H NMR (CDCl$_3$, δppm): --

Column 55,  
Line 53, replace "1H-NMR (CLCl3, δppm):" with -- 1H-NMR (CDCl3, δppm): --

Column 58,  
Line 26, replace "hydrazine (4.52g)" with -- hydrazine hydrate (4.62g) --.

Column 62,  
Line 1, insert -- NMR data --

UNITED STATES PATENT AND TRADEMARK OFFICE
CERTIFICATE OF CORRECTION

PATENT NO.    : 6,342,516 B1
DATED         : January 29, 2002
INVENTOR(S)   : Nobuhiro Umeda et al.

It is certified that error appears in the above-identified patent and that said Letters Patent is hereby corrected as shown below:

Column 63,
Line 27, Compound No. 3-10, under "Total cholesterol", replace "35" with -- 36 --.
Line 57, under heading "Compound No.", replace "4-48"" with -- 4-58 --.

Column 67,
Line 48, replace "existing (C) formula" with -- 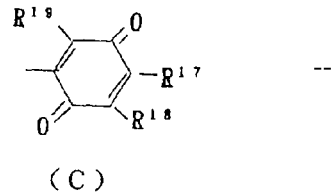 --

Column 68,
Line 3, replace "#—CH=CHCH=—CH—#" with -- #—CH=CHCH=CH—# --
Line 34, replace "existing (3) formula" with -- HOOC-B-Y-Z                    (3) --
Line 55, replace "R" with -- B --.

Signed and Sealed this

Twenty-fourth Day of June, 2003

JAMES E. ROGAN
*Director of the United States Patent and Trademark Office*